(12) United States Patent
Ji et al.

(10) Patent No.: US 11,237,371 B2
(45) Date of Patent: *Feb. 1, 2022

(54) VIDEO-RATE VOLUMETRIC FUNCTIONAL IMAGING OF THE BRAIN AT SYNAPTIC RESOLUTION

(71) Applicant: Howard Hughes Medical Institute, Ashburn, VA (US)

(72) Inventors: Na Ji, Ashburn, VA (US); Rongwen Lu, Ashburn, VA (US)

(73) Assignee: Howard Hughes Medical Institute, Ashburn, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/949,196

(22) Filed: Oct. 19, 2020

(65) Prior Publication Data

US 2021/0048657 A1 Feb. 18, 2021

Related U.S. Application Data

(63) Continuation-in-part of application No. 16/782,557, filed on Feb. 5, 2020, now Pat. No. 10,809,510, which
(Continued)

(51) Int. Cl.
*G01N 21/64* (2006.01)
*G02B 21/00* (2006.01)
(Continued)

(52) U.S. Cl.
CPC ........... *G02B 21/008* (2013.01); *G02B 5/001* (2013.01); *G02B 21/0032* (2013.01);
(Continued)

(58) Field of Classification Search
CPC .............. G02B 21/008; G02B 21/0032; G02B 21/0048; G02B 21/0056; G02B 5/001;
(Continued)

(56) References Cited

U.S. PATENT DOCUMENTS 5,260,578 A 11/1993 Bliton et al.
9,201,008 B2 * 12/2015 Theriault ............... G01N 21/64
(Continued)

OTHER PUBLICATIONS

Ahrens, et al., "Whole-brain functional imaging at cellular resolution using light-sheet microscopy", Nat Meth 10, 2013, pp. 413 420.
(Continued)

*Primary Examiner* — Howard D Brown, Jr.
(74) *Attorney, Agent, or Firm* — Brake Hughes Bellermann LLP

(57) ABSTRACT

A scanning microscope includes a light source for generating a light beam having a wavelength, λ, and beam-forming optics configured for receiving the light beam and generating a quasi-Bessel excitation beam that is directed into a sample. The quasi-Bessel beam has a lateral FWHM and an axial FWHM that is greater than ten times the lateral FWHM, and the beam-forming optics include an excitation objective having an axis oriented in a first direction. The microscope includes beam scanning optics configured for scanning the quasi-Bessel beam in one or more directions that are substantially perpendicular to the first direction, and a detector configured for detecting signal light received from positions within the sample that are illuminated by the quasi-Bessel beam. The signal light is generated in response to an interaction of the excitation beam with the sample, and the signal light is imaged, at least in part, by the excitation objective, onto the detector.

32 Claims, 15 Drawing Sheets

Related U.S. Application Data is a continuation of application No. 15/893,204, filed on Feb. 9, 2018, now Pat. No. 10,578,849.

(60) Provisional application No. 62/456,999, filed on Feb. 9, 2017.

(51) Int. Cl.
 *G02B 5/00* (2006.01)
 *A61B 1/00* (2006.01)

(52) U.S. Cl.
 CPC ..... *G02B 21/0048* (2013.01); *G02B 21/0056* (2013.01); *G02B 21/0076* (2013.01); *A61B 1/00172* (2013.01); *G02B 21/0064* (2013.01)

(58) Field of Classification Search
 CPC ............ G02B 21/0076; G02B 21/0064; G02B 2207/113; G02B 27/58; G02B 26/0825; G02B 26/06; A61B 1/00172
 See application file for complete search history.

(56) References Cited

U.S. PATENT DOCUMENTS

| | | | |
|---|---|---|---|
| 10,578,849 | B2 | 3/2020 | Ji et al. |
| 2011/0006231 | A1 | 1/2011 | Betzig et al. |
| 2011/0096337 | A1* | 4/2011 | Hirose ............... G02B 26/06 356/491 |
| 2011/0122488 | A1 | 5/2011 | Truong et al. |
| 2013/0181143 | A1 | 7/2013 | Betzig et al. |
| 2016/0124222 | A1* | 5/2016 | Huang ............... G02B 27/0068 250/201.9 |
| 2017/0343784 | A1 | 11/2017 | Wu et al. |

OTHER PUBLICATIONS

Andermann, et al., "Chronic cellular imaging of mouse visual cortex during operant behavior and passive viewing", Frontiers in Cellular Neuroscience, vol. 4, Article 3, Mar. 2010, pp. 1-16.
Botcherby, et al., "Scanning two photon fluorescence microscopy with extended depth of field", Optics Communications 268, 2006, pp. 253-260.
Bouchard, et al., "Swept confocally-aligned planar excitation (SCAPE) microscopy for high-speed volumetric imaging of behaving organisms", Nat Photon 9, Feb. 2015, pp. 113-119.
Chen, et al., "Ultrasensitive fluorescent proteins for imaging neuronal activity", Nature 499, 2013, pp. 295-300.
Denk, et al., "Two-Photon Laser Scanning Fluorescence Microscopy", Science, New Series, vol. 248, No. 4951, Apr. 6, 1990, pp. 73-76.
Dombeck, et al., "Imaging Large-Scale Neural Activity with Cellular Resolution in Awake, Mobile Mice", Neuron 56, 2007, pp. 43-57.
Goebel, et al., "In Vivo Calcium Imaging of Neural Network Function", Physiology 22, 2007, pp. 358-365.
Greenberg, et al., "Automated correction of fast motion artifacts for two-photon imaging of awake animals", Journal of Neuroscience Methods 176, 2009, pp. 1-15.
Jenett, et al., "A GAL4-driver line resource for *Drosophila* neurobiology", Cell Rep. 2, 2012, pp. 991-1001.
Ji, et al., "High-speed, low-photodamage nonlinear imaging using passive pulse splitters", Nature methods 5, 2008, pp. 197-202.
Ji, et al., "Technologies for imaging neural activity in large volumes", Nat Neurosci 19, 2016, pp. 1154-1164.
Jia, et al., "Dendritic organization of sensory input to cortical neurons in vivo", Nature 464, Apr. 29, 2010, pp. 1307-1132.
Liu, et al., "Laser Ablations Reveal Functional Relationships of Segmental Hindbrain Neurons in Zebrafish", Neuron, vol. 23, Jun. 1999, pp. 325-335.
O'malley, et al., "Imaging the Functional Organization of Zebrafish Hindbrain Segments during Escape Behaviors", Neuron 17, 1996, pp. 1145-1155.
Panier, et al., "Fast functional imaging of multiple brain regions in intact zebrafish larvae using Selective Plane Illumination Microscopy", Frontiers in Neural Circuits 7, 2013, 11 pages.
Pnevmatikakis, et al., "Simultaneous Denoising, Deconvolution, and Demixing of Calcium Imaging Data", Neuron 89, 2016, pp. 285-299.
Podgorski, et al., "Brain heating induced by near infrared lasers during multi-photon microscopy", J Neurophysiol 116, 2016, pp. 1012-1023.
Pologruto, et al., "ScanImage: Flexible software for operating laser scanning microscopes", BioMedical Engineering OnLine 2, 2003, pp. 1-9.
Schindelin, et al., "Fiji: an open-source platform for biological-image analysis", Nat Meth 9, 2012, pp. 676-682.
Schneider, et al., "NIH Image to ImageJ: 25 years of image analysis", Nat Meth 9, 2012, pp. 671-675.
Seelig, et al., "Two-photon calcium imaging from head-fixed *Drosophila* during optomotor walking behavior", Nat Meth 7, 2010, pp. 535-540.
Sheppard, et al., "Imaging properties of annular lenses", Applied Optics, vol. 18, Nov. 15, 1979, pp. 3764-3769.
Song, et al., "Volumetric Two-photon Imaging of Neurons Using Stereoscopy (vTwINS)", bioRxiv, 2016.
Svoboda, et al., "Principles of Two-Photon Excitation Microscopy and Its Applications to Neuroscience", Neuron 50, Jun. 15, 2006, pp. 823-839.
Thériault, et al., "Extended depth of field microscopy for rapid volumetric two-photon imaging", Optical Society of America, vol. 21, No. 8, Apr. 22, 2013, 10 pages.
Thériault, et al., "Extended two-photon microscopy in live samples with Bessel beams: steadier focus, faster volume scans, and simpler stereoscopic imaging", Frontiers in Cellular Neuroscience, vol. 8, No. 139, May 20, 2014, 11 pages.
Thiele, et al., "Descending Control of Swim Posture by a Midbrain Nucleus in Zebrafish", Neuron 83, Aug. 6, 2014, pp. 679-691.
Welford, "Use of Annular Apertures to Increase Focal Depth", Journal of the Optical Society of America, vol. 50, No. 8, Aug. 1960, pp. 749-753.
Yang, et al., "Simultaneous Multi plane Imaging of Neural Circuits", Neuron 89, 2016, pp. 269-284.

* cited by examiner

900

910

920

930

940

Bimorph deformable
mirror
(Cross section view)

VIDEO-RATE VOLUMETRIC FUNCTIONAL IMAGING OF THE BRAIN AT SYNAPTIC RESOLUTION

CROSS-REFERENCE TO RELATED APPLICATIONS

This application is a continuation in part of, and claims priority to, U.S. patent application Ser. No. 16/782,557, filed on Feb. 5, 2020, entitled "VIDEO-RATE VOLUMETRIC FUNCTIONAL IMAGING OF THE BRAIN AT SYNAPTIC RESOLUTION", which claims priority to U.S. patent application Ser. No. 15/893,204, filed on Feb. 9, 2018, entitled "VIDEO-RATE VOLUMETRIC FUNCTIONAL IMAGING OF THE BRAIN AT SYNAPTIC RESOLUTION", now U.S. Pat. No. 10,578,849, which claims priority to U.S. Provisional Patent Application No. 62/456,999, filed on Feb. 9, 2017, entitled "VIDEO-RATE VOLUMETRIC FUNCTIONAL IMAGING OF THE BRAIN AT SYNAPTIC RESOLUTION," the disclosures of which are incorporated herein by reference in their entirety.

TECHNICAL FIELD

This description relates to optical microscopy and, in particular, to video-rate volumetric functional imaging of the brain at synaptic resolution.

BACKGROUND

Biological structures (e.g., neurons and neural networks) often extend hundreds to thousands of micrometers in three dimensions. Understanding neural computation requires the ability to measure how a neuron integrates its multitude of synaptic inputs, as well as how neural ensembles work together during sensory stimulation and motor control. With submicron lateral resolution and optical sectioning ability in scattering brains, two-photon laser scanning microscopy (2PLSM) is a powerful tool for monitoring the activity of neurons and their networks in vivo through their calcium transients. However, both individual neurons and neural networks may extend over hundreds or even thousands of micrometers in three dimensions. To view temporal dynamics of their activity (e.g., calcium transients associated with their activity) volume imaging methods with sub-second temporal resolution are needed. However, such speed is difficult to achieve with conventional two-photon laser scanning microscopy (2PLSM), because of the dependence of 2PLSM on serial focal scanning in three dimensions (3D) and the limited brightness of indicators. Because conventional 2PLSM images volume by scanning the excitation laser focus serially in 3D, the limited brightness of calcium indicators and the inertia of laser scanning units make it difficult to capture all the calcium transients in a volume at video rate (e.g., 30 Hz) while maintaining the ability to resolve synaptic structures such as dendritic spines and axonal boutons.

Thus, what is desired are techniques for high-speed, high-resolution imaging of large specimens.

SUMMARY

In a first general aspect, a scanning microscope includes a light source for generating a light beam having a wavelength, $\lambda$, and beam-forming optics configured for receiving the light beam and generating a quasi-Bessel excitation beam that is directed into a sample. The quasi-Bessel beam has a lateral FWHM and an axial FWHM that is greater than ten times the lateral FWHM, and the beam-forming optics include an excitation objective having an axis oriented in a first direction. The microscope includes beam scanning optics configured for scanning the quasi-Bessel beam in one or more directions that are substantially perpendicular to the first direction, and a detector configured for detecting signal light received from positions within the sample that are illuminated by the quasi-Bessel beam. The signal light is generated in response to an interaction of the excitation beam with the sample, and the signal light is imaged, at least in part, by the excitation objective, onto the detector.

Implementations can include one or more of the following features, alone or in any combination with each other. For example, the axial FWHM can be greater than 15 micrometers and the lateral FWHM can be less than one micrometer. The signal light can have a wavelength of $\lambda/2$. The signal light can be generated though a non-linear signal generation process during the interaction of the quasi-Bessel beam with the sample. The signal light can include fluorescence light emitted from the sample after excitation by the quasi-Bessel beam.

The microscope can include an annular mask in a path of the light beam, which is configured to generate an annular ring of light from which the quasi-Bessel beam is formed. The beam forming optics can include a spatial light modulator (SLM) configured to receive the light beam and to generate the quasi-Bessel beam in the sample. The SLM can include a binary spatial light modulator (SLM). The beam scanning optics can be configured for repeatedly scanning the quasi-Bessel beam over an area substantially perpendicular to the first direction at a rate greater than 10 Hz.

In another general aspect, a method of imaging a sample includes receiving a light beam having a wavelength, $\lambda$, and transforming the received light beam into a quasi-Bessel excitation beam propagating in a first direction in the sample, where the quasi-Bessel beam has a lateral FWHM and an axial FWHM that is greater than ten times the lateral FWHM. The quasi-Bessel beam is scanned in one or more directions that are substantially perpendicular to the first direction, and signal light received from positions within the sample that are illuminated by the quasi-Bessel beam is detected, where the signal light is generated in response to an interaction of the excitation beam with the sample. The quasi-Bessel beam is provided through an excitation objective to the sample, and the detected signal light is received though the excitation objective and generating an image of the sample based on the detected signal light.

Implementations can include one or more of the following features, alone or in any combination with each other. For example, generating the image of the sample can include generating a two-dimensional image of the sample, where the two-dimensional image corresponds to a projection of features in the sample that emit signal light when the quasi-Bessel beam is scanned in the one or more directions that are substantially perpendicular to the first direction without translating the quasi-Bessel beam along the first direction. The axial FWHM can be greater than 15 micrometers and the lateral FWHM is less than one micrometer. The signal light can have a wavelength of $\lambda/2$. The signal light can be generated though a non-linear signal generation process during the interaction of the quasi-Bessel beam with the sample. The signal light can include fluorescence light emitted from the sample after excitation by the quasi-Bessel beam. Transforming the received light beam into the quasi-Bessel can include reflecting the received light beam off a spatial light modulator (SLM) that modifies the wavefront of the received light beam. The SLM can include a binary phase SLM. Scanning the quasi-Bessel beam can include repeatedly scanning the quasi-Bessel beam over an area substantially perpendicular to the first direction at a rate greater than 10 Hz.

In another general aspect, an apparatus is adapted for coupling to an laser scanning microscope that includes (a) a light source for generating an excitation light beam having a wavelength, λ, (b) beam scanning optics configured for scanning the light beam in one or more directions that are perpendicular to a propagation direction of the beam in the sample, (c) an excitation objective having an axis oriented along the propagation direction and being configured for focusing the excitation light beam in the sample, and (d) a detector configured for detecting signal light received from positions within the sample that are illuminated by the beam, where the signal light is generated in response to an interaction of the excitation beam with the sample and wherein the signal light is imaged, at least in part, by the excitation objective, onto the detector. The apparatus includes beamforming optics configured for receiving the light beam and modifying the received light to generate a quasi-Bessel excitation beam in the sample, wherein the quasi-Bessel beam has a lateral FWHM and an axial FWHM that is greater than ten times the lateral FWHM, one or more first beam handling optical elements configured for receiving the light beam and providing the light beam to the beam forming optics, and one or more second beam handling optical elements configured for receiving the modified light beam and providing the light beam to the beam scanning optics for scanning the quasi-Bessel beam in the sample.

Implementations can include one or more of the following features, alone or in any combination with each other. For example, the axial FWHM can be greater than 15 micrometers and the lateral FWHM can be less than one micrometer. The signal light can have a wavelength of $\lambda/2$. The signal light can be generated though a non-linear signal generation process during the interaction of the quasi-Bessel beam with the sample. The signal light can include fluorescence light emitted from the sample after excitation by the quasi-Bessel beam.

The apparatus can also include an annular mask in a path of the light beam and that is configured to generate an annular ring of light from which the quasi-Bessel beam is formed. The beam forming optics can include a spatial light modulator (SLM) configured to receive the light beam and to generate the quasi-Bessel beam in the sample. The SLM can include a binary SLM. The beam scanning optics can be configured for repeatedly scanning the quasi-Bessel beam over an area substantially perpendicular to the first direction at a rate greater than 10 Hz.

The details of one or more implementations are set forth in the accompanying drawings and the description below. Other features will be apparent from the description and drawings, and from the claims.

DETAILED DESCRIPTION

Described herein are systems and methods for imaging samples by scanning an axially elongated quasi-Bessel focus in two dimensions to image a volume of a sample at the rate at which the focus is scanned in the two dimensions and thereby enabling video-rate volumetric imaging. Using quasi-Bessel foci designed to maintain a high lateral resolution that resolves synapses in vivo, temporal dynamics of biological specimens (e.g., calcium dynamics of volumes of neurons and synapses in fruit flies, zebrafish larvae, mice, and ferrets) can be imaged in vivo. In addition, the systems can be created in an optical module that can be easily integrated into standard 2PLSMs to perform the techniques described herein.

For many in vivo brain imaging experiments, the positions of neurons as well as their synapses are known and remain unchanged during each imaging session. Thus, it may be unnecessary to constantly monitor and track the positions of the neurons and synapses in 3D during imaging of temporal dynamics of the structures. Therefore, by relaxing the requirement of monitoring and tracking the positions of neurons and synapses in 3D, volume imaging speed can be increased substantially by sacrificing axial resolution in the imaging apparatus. Because typical excitation laser beams having a Guassian intensity profile in the direction perpendicular to the propagaussion direction of the beam are focused to a spot having axial and lateral extents that are correlated, sacrificing axial resolution in such a beam would also sacrifice lateral resolution. However, by scanning an axially elongated focus (e.g., a quasi-Bessel beam) in two dimensions (2D), projected views of 3D volumes can be obtained and 2D frame rates can be converted into 3D volume rates, while still maintaining high lateral resolution.

To understand information processing in neurons and neural networks that extend in three dimensions, the techniques described herein can be used to record neural activity with sub-second volume rates, while maintaining sufficient lateral resolution to resolve individual synapses. Taking advantage of the fact that, during most in vivo brain imaging experiments, the structures of interest are stationary, volume information can be obtained by scanning in 2D an axially extended focus approximating a Bessel beam. Using quasi-Bessel foci optimized to maintain high lateral resolution in vivo, living biological samples (e.g., brains of a variety of species, including fruit fly, zebrafish, mouse, and ferret) can be imaged at a video rate to recover high-speed volumetric imaging of neurons and neural compartments in vivo. Preserving submicron, synapse-resolving lateral resolution while reducing the background generated by the outer rings of the quasi-Bessel beams, these quasi-Bessel foci permit measuring calcium activity from single spines on multiple dendritic branches at at least 30 Hz.

Figure 1:
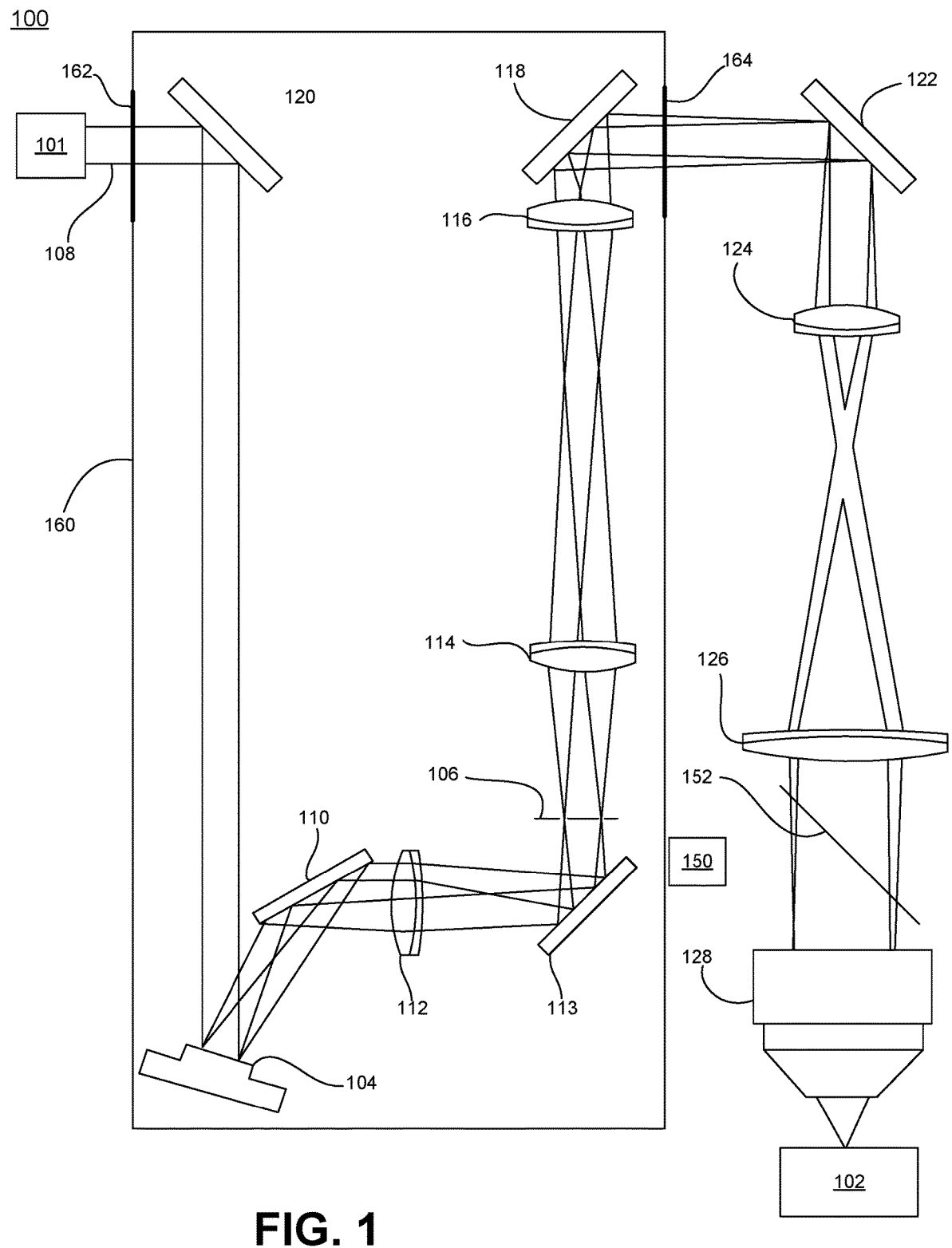
FIG. 1 is a schematic diagram of a microscopy system for creating video images of a volume of a sample.

FIG. 1 is a schematic diagram of a microscopy system 100 for creating video images of a volume of a sample 102. The system 100 can include a spatial light modulator (SLM) 104 and an annular apodization mask 106 and can receive excitation light 108 from a laser 101, where the SLM 104 can modify the received excitation light before providing it to the sample 102. In some implementations, the annular mask 106 can be selected from an array of different masks, for example, a rotatable array that permits different masks to be rotated and position at the location of the mask 106. The received light can be reflected off of a mirror 120 before being provided to the SLM 104. Light modified by the SLM 104 can be reflected off a first mirror 110, focused by a lens 112, and reflected by a second mirror 113 to a focal plane of the lens located at the annular mask 106. A concentric binary phase pattern on the SLM 104 can be used to generate a ring of illumination at the focal plane of lens 112.

With the SLM placed at the front focal plane of lens 112, an electric field distribution that is the Fourier transform of the phase pattern on the SLM is generated at the back focal plane of lens 112, where the annular apodization mask 106 is placed to block spurious orders and undiffracted light. After spatial filtering by the annular mask 106, the ring pattern at the annular apodization mask 106 can be imaged by lenses 114, 116 and reflected off the mirror 118 onto a plurality of galvanometer scanners 122 that can be used to scan the excitation beam in the X-Y directions (i.e., perpendicular to the direction of the beam) in the sample 102. In some implementations, patterns can be applied to the SLM to translate/scan the expectation beam in the X-Y directions (as well as the Z direction), and with steering of the beam by the SLM, galvanometer scanners may be unnecessary. Light from the galvanometer scanners 122 can be imaged by one or more pairs of lenses 124, 126 onto a back pupil plane of a microscope objective 128 that focuses the excitation light onto the sample 102.

This configuration can provide an annular illumination on the back pupil plane of the microscope objective 128 and an axially extended focus approximating a Bessel beam within the sample 102. By using different SLM patterns with distinct annular masks, a series of quasi-Bessel foci with different axial full widths at half maximum (FWHM) (i.e., the length of the quasi-Bessel beam focus in the axial direction of the beam between the locations at which the beam has half the maximum intensity in the focus) can be provided to the sample 102. The SLM also can be used to control the lateral FWHM of the beam. In a quasi-Bessel beam, the axial FWHM of the beam is more than ten times the lateral FWHM of the beam (i.e., the width of the quasi-Bessel beam focus in the direction perpendicular to the propagation direction of the beam between the locations at which the beam has half the maximum intensity in the focus). In some implementations, the axial FWHM can be about 15 to 400 μm and the numeric aperture (NA) of the beam at the back pupil of the objective 128 can be about 0.2 to 0.93.

As the excitation beam is scanned in the X-Y directions through the sample 102 by the galvanometer scanners 122, molecules in the sample can be excited by the beam and caused to emit signal light at the X-Y location at which they are excited by the excitation beam. The signal light can be generated through a nonlinear excitation process. For example, multiple photons of excitation light can be absorbed by a molecule in the sample, and then the molecule can emit signal light having a wavelength that is, for example, two times or three times the wavelength of the excitation light. The signal light can be focused by the objective lens 128 and provided to a detector 150 (e.g., by reflecting the signal light off a beam splitter or wavelength selective mirror 152) that records the signal light as a function of the X-Y location of the excitation beam. By collecting the signal light as a function of the location of the excitation beam, information can be collected and processed (e.g., by a processor) to generate an image of the sample 102.

Because high-NA quasi-Bessel foci have relatively large amounts of energy distributed in their side rings compared to low-NA quasi-Bessel foci, a substantial background signal due to excitation by the side rings can occur and cause image blur, even with suppression by nonlinear excitation. Because the central peak of a quasi-Bessel focus is sharper in X-Y than that of a Gaussian focus, even at NA 0.4, a quasi-Bessel focus still has sufficient lateral resolution to resolve individual synaptic terminals but generates less background haze than a quasi-Bessel focus having a NA of, for example, 0.93.

The quasi-Bessel foci can be formed in the sample 102 by shaping the wavefront of the excitation laser using a phase-only spatial light modulator (SLM) 104. To generate annular illumination patterns efficiently, circular binary grating patterns composed of concentric rings with phases alternating between 0 and π can be applied to the SLM 104. These grating patterns can diffract most of the excitation light energy into the ±1 diffraction orders, to form a ring at the focal plane of lens 112, where the annular mask 106 is located. The radius of the ring (ρ) can be determined by the period of the grating (d), the focal length of lens 112 ($f_1$), and the wavelength of the light (λ), and can be calculated from the grating equation as:

$$\rho = \frac{f_1 \lambda}{d} \qquad (1)$$

For the annular mask 106 to transmit the ring and block the other diffraction orders, its inner and outer diameters $D_i$ and $D_o$ can be selected such that $$4\rho = D_o + D_i. \qquad (2)$$

Combining the above two equations, to generate an annular illumination pattern that is centered on the annular mask 106 with inner and outer diameters $D_o$ and $D_i$, the period of the circular binary grating on the SLM can be selected to be:

$$d = \frac{4 f_1 \lambda}{D_o + D_i} \qquad (3)$$

With the size of an SLM pixel defined asp, the period of the circular binary grating in units of pixels S can be expressed as:

$$S = \frac{d}{p} = \frac{4 f_1 \lambda}{p(D_o + D_i)}. \qquad (4)$$

Figure 2:
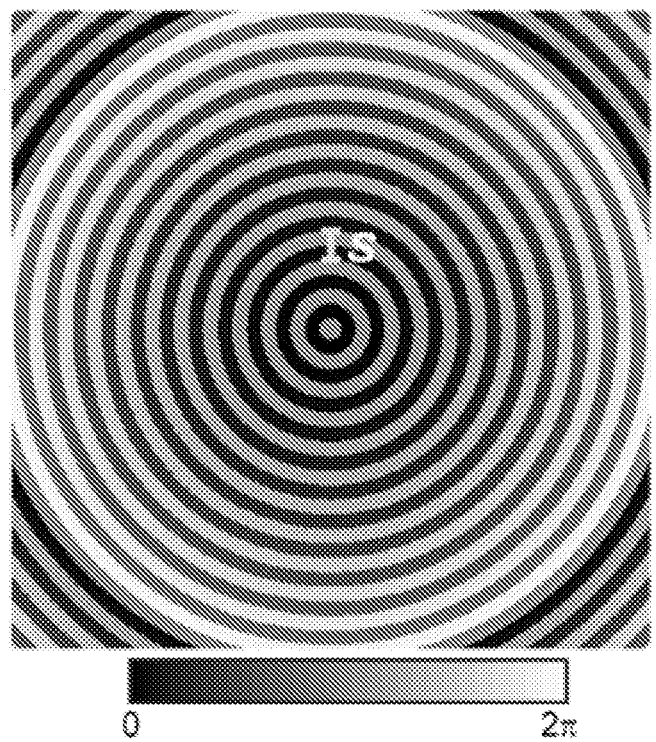
FIG. 2 is an example binary phase pattern that can be applied to a spatial light modulator to generate the quasi-Bessel beam in a sample.

The thickness of the annulus generated by the above circular binary grating is approximately $$d = \frac{2f_1\lambda}{beamD} \quad (5)$$

where beamD is the diameter of the excitation laser on the SLM 104. FIG. 2 shows an example phase pattern that can be applied to the SLM 104 to generate the quasi-Bessel beam in the sample 102. In particular, the phase pattern shown in FIG. 2 includes a binary pattern superimposed on a gray-level pattern that corresponds to defocus of the beam. As indicated by the above equations, both the radius and thickness of the annular illumination are wavelength dependent. For typical commercial femtosecond lasers (pulse widths>65 fs, bandwidth<13 nm for 900 nm output), dispersion affects the generation of annular illumination minimally.

In some implementations, optical elements for converting a Gaussian beam into a quasi-Bessel beam can be provided in a self-contained module 160 that can be retrofitted onto an existing microscope system that ordinarily provides a Gaussian beam to the sample 102. For example, the module 160 can include windows 162, 164 through which the Gaussian beam can enter the module 160 and through which the modified beam that results in the quasi-Bessel beam within the sample can exit the module, respectively. The optical elements within the module 160 can include the SLM 104, the annular mask 106, lenses 112, 114, 116 and mirrors 120, 110, 118. In some implementations, mirrors 120, 118 can be movable, such that they can be moved out of the way of the path of the Gaussian beam 108 so that the Gaussian beam can pass through the module 160 without any modification and then can be provided to the sample 102.

To add the module 160 into an existing two-photon microscopy system, once the SLM 104 and objective 128 are selected, optical elements and parameters in the rest of the light path (e.g., focal lengths of lenses 112, 114, 116, the beam diameter beamD, and $D_i$ and $D_o$ of the annular mask 106) can be designed to obtain quasi-Bessel foci of desired NAs and axial lengths within the sample 102. The focal lengths $f_3$ and $f_2$ of lenses 116 and 114, respectively, contribute to the magnification factor mp, where mp is the product of $f_3/f_3$ and the magnification between the galvo scanners and back pupil of the objective 128. To generate a quasi-Bessel beam of a specific NA (desiredNA), the annular illumination pattern on the objective back pupil can have an outer diameter that is the product of desiredNA and the objective focal length. De-magnifying by mp, we obtain the outer diameter of the annular mask, $D_o$.

The axial length of the quasi-Bessel beam is dictated by the thickness of the ring, which is determined by the focal length of lens 112 and the beam diameter on SLM 104, with a smaller focal length and larger beam diameter generating thinner rings and longer quasi-Bessel foci. The axial length of the focus of the quasi-Bessel beam can be further adjusted by fine-tuning $D_i$ and S (and $D_o$, if the NA of the quasi-Bessel focus is allowed to vary).

Figure 3:
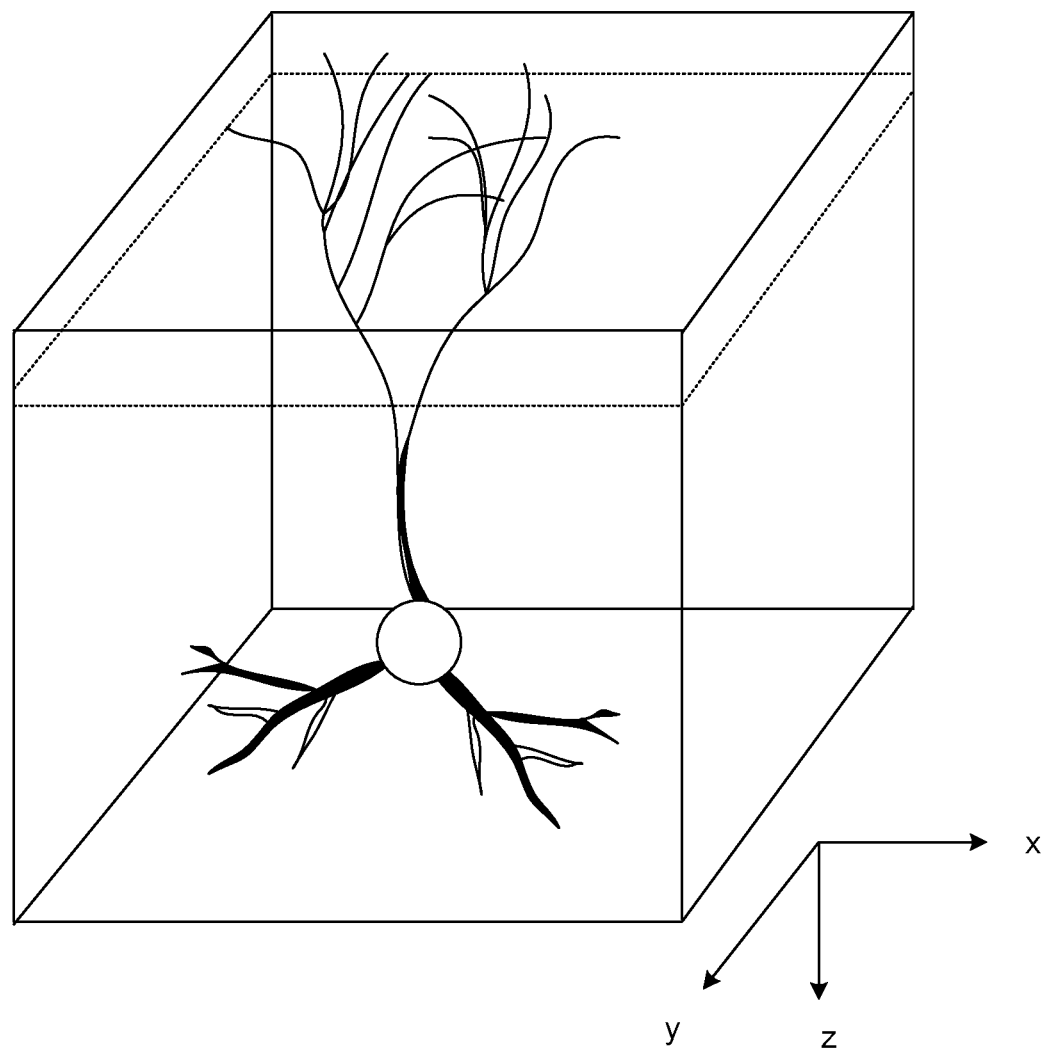
FIG. 3 is a schematic diagram of a biological sample that is imaged by scanning a focused Gaussian beam in a plane perpendicular to the axial direction of the beam.
Figure 4:
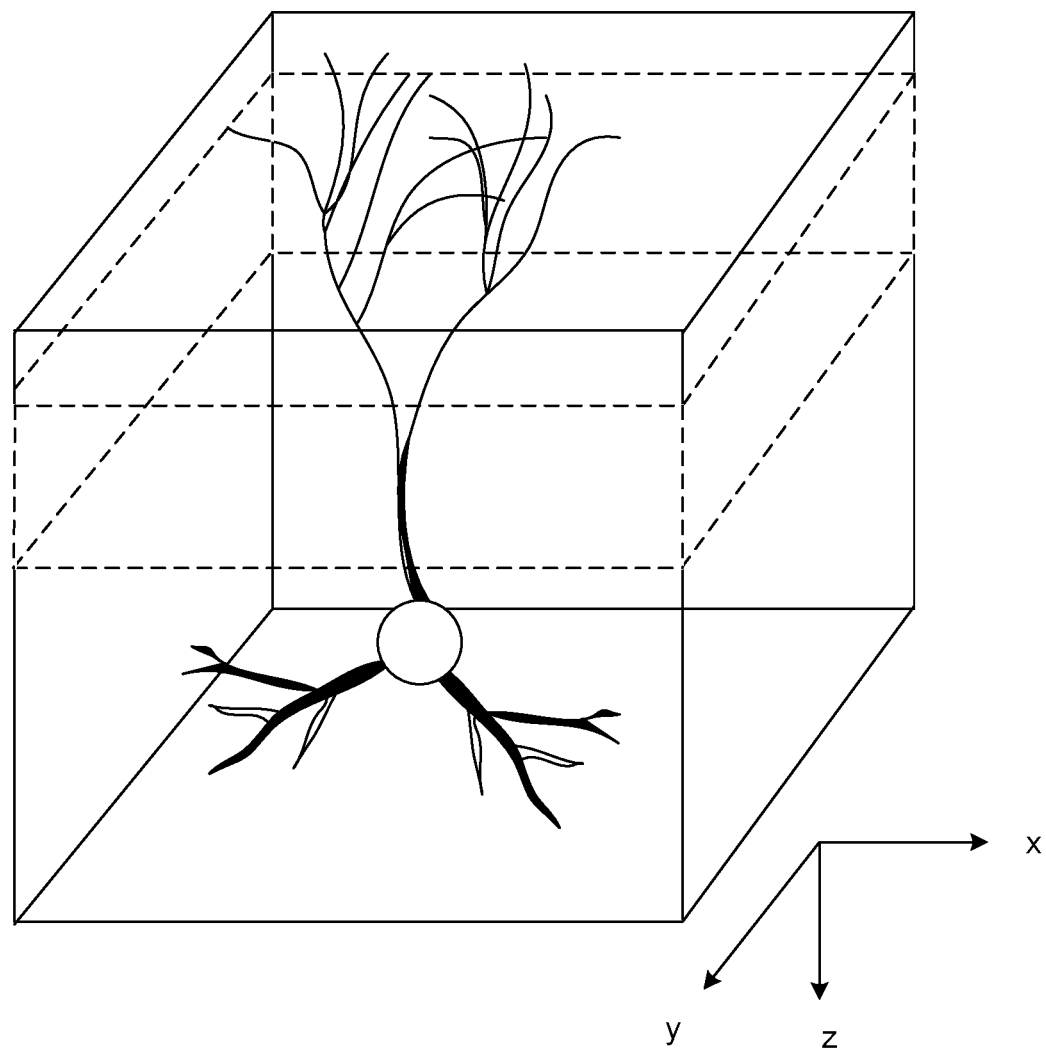
FIG. 4 is a schematic diagram of a biological sample that is imaged by scanning a focused quasi-Bessel beam in in a plane perpendicular to the axial direction of the beam.

A difference between the volume of a sample imaged by scanning a Gaussian beam in the X-Y direction versus scanning the quasi-Bessel beam in X-Y direction can be seen from a comparison of FIG. 3, which is a schematic diagram of a biological sample that is imaged by scanning a focused Gaussian beam in XY, with FIG. 4, which is a schematic diagram of a biological sample that is imaged by scanning a focused quasi-Bessel beam in X-Y. As shown in FIG. 3, when the sample is excited by a Gaussian beam having a beam waist, w, and the beam is scanned in X-Y, a volume having a thickness in in the z direction corresponding to the axial FWHM of the beam can be imaged in the sample. As shown in FIG. 4, when the sample is excited by a quasi-Bessel beam having a beam waist, w, and the beam is scanned in X-Y, a volume having a thickness in in the z direction corresponding to the axial FWHM of the beam can be imaged in the sample, where the thickness of the volume for the quasi-Bessel beam is much greater than the thickness of the volume for the Gaussian beam, because the axial FWHM of the quasi-Bessel beam is greater than that of the Gaussian beam.

To visualize temporal dynamics of features within a sample, a relatively large volume of the sample can be scanned with the quasi-Bessel beam. In some implementations, high resolution values of the coordinates of features within the sample first can be obtained by a scanning a Gaussian beam in the X-Y directions at different depths in Z. With the higher Z-axis resolution of the Gaussian beam, high resolution values of the position of a feature within the sample can be obtained. Then, for samples in which the features move relatively little over time, the sample can be volume scanned with a quasi-Bessel beam to observe temporal dynamics of the features. The temporal activity of a feature that emits light in response to the scanned quasi-Bessel beam excitation light can be observed by the occurrence of a signal light from an X-Y position that had previously been associated with the feature, for example, that had been associated with the feature during scanning of the sample by the Gaussian beam. Even when two features located at different Z-axis positions but having overlapping X-Y positions are active, the temporal activity of the two features can be distinguished based on correlations of their activity with activity of other features within the sample. For example, activity of a first synapse located at $(x_1, y_1, z_1)$ may be correlated with activity of a feature located at $(x_2, y_2, z_2)$, and activity of a second synapse located at $(x_1, y_1, z_3)$ may be correlated with activity of a feature located at $(x_3, y_3, z_4)$, where $(x_1, y_1)$ is resolvable from $(x_3, y_3)$. Thus, even though the first and second synapse have the same X-Y coordinates and may not be resolved in the Z-direction by a quasi-Bessel beam having a large axial FWHM, the activity of the first and second synapses may nevertheless be distinguished in the quasi-Bessel beam volume scan based on the correlation of the activity observed at $(x_1, y_1)$ with signal light received from other X-Y locations in the volume scan.

Figure 7:
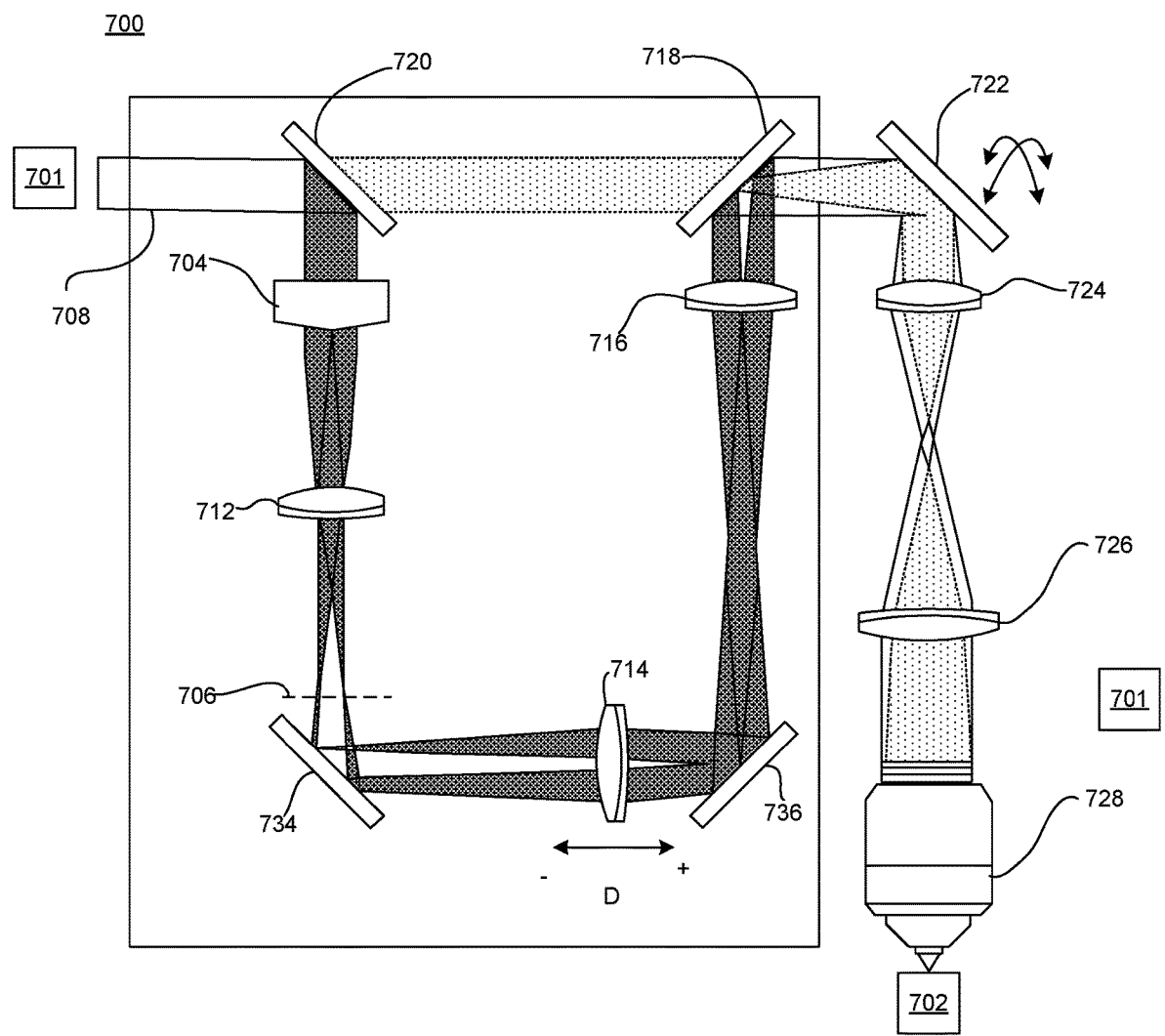
FIG. 7 is another schematic diagram of a microscopy system for creating video images of a volume of a sample.

FIG. 7 is another schematic diagram of a microscopy system 700 for creating video images of a volume of a sample 702 in which an axicon 704, rather than an SLM, can serve as an optical element for creating a quasi-Bessel beam within the sample. The system 700 can include an axicon 704 and can receive excitation light 708 from a laser 701. The axicon 704 can modify the received excitation light before providing it to the sample 702. The received light can be reflected off of a mirror 720 before being provided to the axicon 704. Light modified by the axicon 704 can be imaged by a lens 712 onto a focal plane located at which an optional annular apodization mask 706 can be located for blocking unwanted light due to imperfections in the axicon. After spatial filtering by the annular mask 706, the ring pattern created by the axicon can be imaged by lenses 714, 716 and reflected off the mirror 718 onto plurality of galvanometer scanners 722 that can be used to scan the excitation beam in the X-Y directions (i.e., perpendicular to the direction of the beam) in the sample 702. Light from the galvanometer scanners 722 can be imaged by one or more pairs of lenses 724, 726 onto a back pupil plane of a microscope objective 728 that focuses the excitation light onto the sample 702. This configuration can provide an annular illumination on the back pupil plane of the microscope objective 728 and an axially extended focus approximating a Bessel beam within the sample 702.

To obtain different quasi-Bessel foci with different axial FWHMs, lens 714 can be translated along the beam path between mirrors 734 and 736. When the displacement of lens 714 is negative (i.e., moving lens 714 closer to the mask), more power is allocated to the central region of the objective back focal plane, which yields a smaller effective NA and, together with the phase distribution of the pupil function, a longer Bessel focus. In contrast, moving the lens away from the mask 706 distributes more power to the edge of the objective pupil function, leading to a bigger effective NA and a shorter focus. This way, moving the lens from left to right in FIG. 7 can continuously change the lateral and axial FWHMs of the quasi-Bessel beam. It is worth noting that there is a tradeoff between axial/lateral FWHM and the peak signal. Given the same power at the axicon 704, longer Bessel foci (obtained by translation lens 714 toward mask 706) have larger lateral FWHMs and smaller peak signals, because there is less energy in the central peak of the foci. For the shortest Bessel foci, light can begin to be clipped by the objective, leading to a decrease in the post-objective power. By translating lens 716 along the beam path it is also possible to obtain different quasi-Bessel foci with different axial FWHMs.

Regardless of how a quasi-Bessel beam focus is generated in the sample, once incorporated into a microscope, the volume imaging speed depends on the lateral scanning speed of the microscope, with 30 Hz volume rate at 512×512 lateral pixels easily achievable in systems equipped with resonant galvos or acousto-optic deflectors. With these systems, much higher volume speed can be achieved by simply reducing the number of lateral pixels. Ultimately, with heating and photodamage of the sample placing an upper limit on excitation power, the practically achievable volume imaging speed depends on the fluorescence probe, with brighter probes requiring less dwell time at each pixel and thus enabling higher imaging speed.

Foci having different axial FWHM lengths and lateral widths can be created using the quasi-Bessel beams described herein. The practically useful FWHM axial length is determined by both the sample and the desired lateral resolution. Sparsely labeled samples have lower probability of having structures overlap in their xy locations, thus allow longer foci to be used. However, at the same NA, longer Bessel foci have more energy in the side rings surrounding the central peak, which may lead to higher background signal. By relaxing the lateral resolution requirement (e.g., from submicron, synaptic resolution to cellular, micron-level resolution) can allow lower-NA Bessel foci to be employed, where background contamination by the side rings is less of an issue.

Another practical limitation on the length of the Bessel focus is optical power. In general, compared to Gaussian focus scanning, the redistribution of power into the side rings during the formation of a Bessel focus requires the average excitation power to be increased. For large structures such as somata, because the axial extension of the Bessel focus allows a larger volume of fluorophores to be excited, the power increase may be small. Smaller structures such as dendritic spines require higher power increase, and care should be taken to ensure that the sample is not altered by the deposited laser power. However, because in a Bessel focus, the extra power is distributed broadly in the side rings rather than in the central peak, photo-induced damages involving high-order nonlinear processes should not be much more severe than in the case of a Gaussian focus.

Volumetric imaging with quasi-Bessel focus scanning can be used on any sample with sparsely labeled stationary structures. In general, if the volumetric structures of interest can be visualized by the mean intensity projection of their Gaussian image stack, then quasi-Bessel focus scanning can be applied to image the sample. For densely labeled brain specimen, quasi-Bessel beam scanning can be used as a high-throughput screening method to identify areas of activity followed by investigations at higher axial resolution. For studies of densely labeled brains where single neuron resolution is required, Bessel scanning may also be applied, if the activity pattern is sparse and spatially overlapping calcium responses can be unmixed temporally. However, due to the much more extended axial excitation by a quasi-Bessel beam focus, calcium signals measured in the quasi-Bessel focus scanning mode may contain more substantial contribution from neuropils expressing calcium indicator, which should be removed from the final image. Nuclear-targeted calcium indicators may be used to further eliminate this complication.

In some implementations, quasi-Bessel beam focus scanning can employ nonlinear excitation methods (e.g., two- or three-photon excitation), which allow it to be applied to more opaque samples. By projecting 3D volume information into 2D, Bessel focus scanning can lead to a many-fold reduction in data size and orders-of-magnitude increase in image throughput compared to volume imaging methods that rapidly move a Gaussian focus in 3D. In addition, a quasi-Bessel beam focus scanning module can be integrated into existing microscope systems without any change to the data acquisition hardware or software. The intrinsic insensitivity to sample z motion of quasi-Bessel beam focus scanning also makes this extended depth-of-field approach suitable for in vivo volume imaging in awake preparations.

Figure 5:
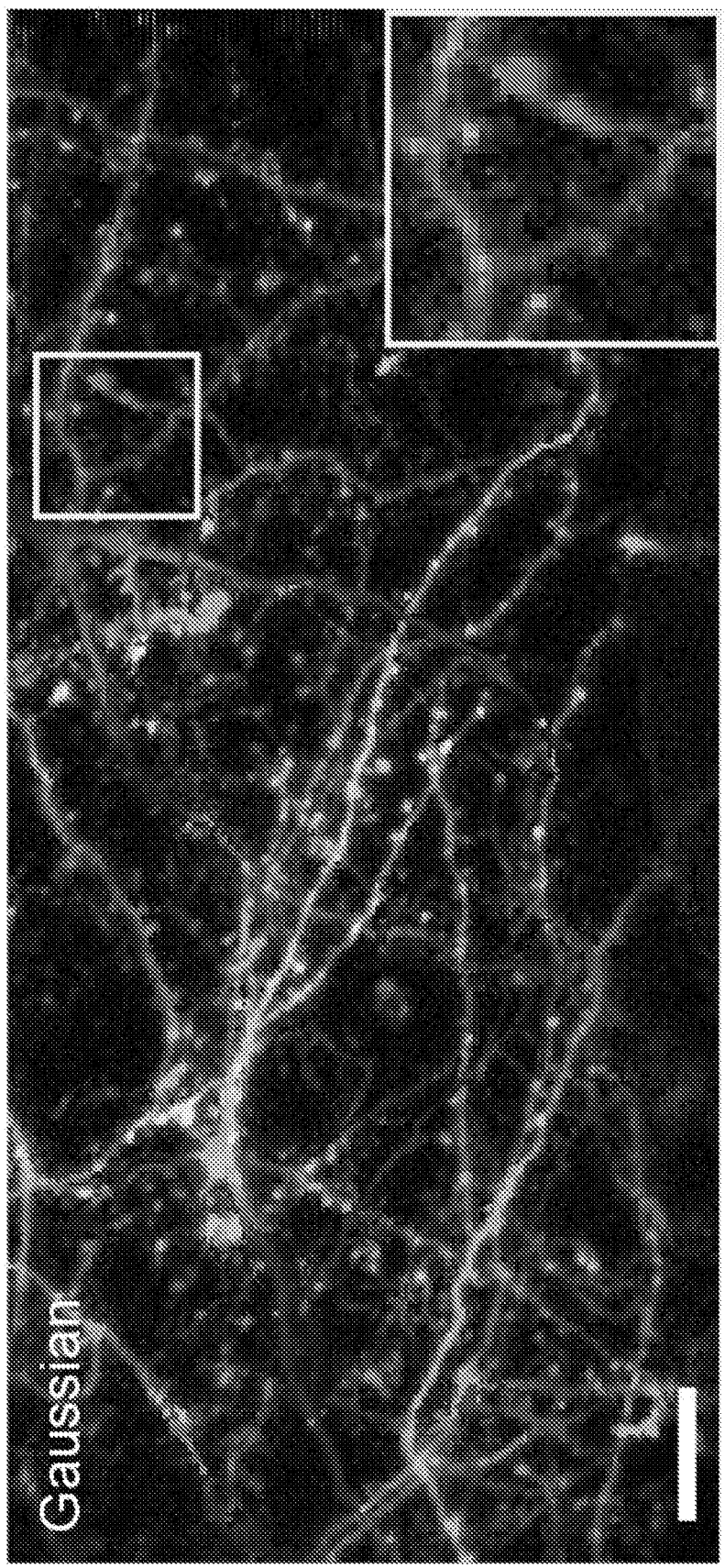
FIG. 5 is an image obtained from projecting onto a single image plane a plurality of two-dimensional image frames obtained by scanning a Gaussian excitation beam through different adjacent parallel planes of a sample.
Figure 6:
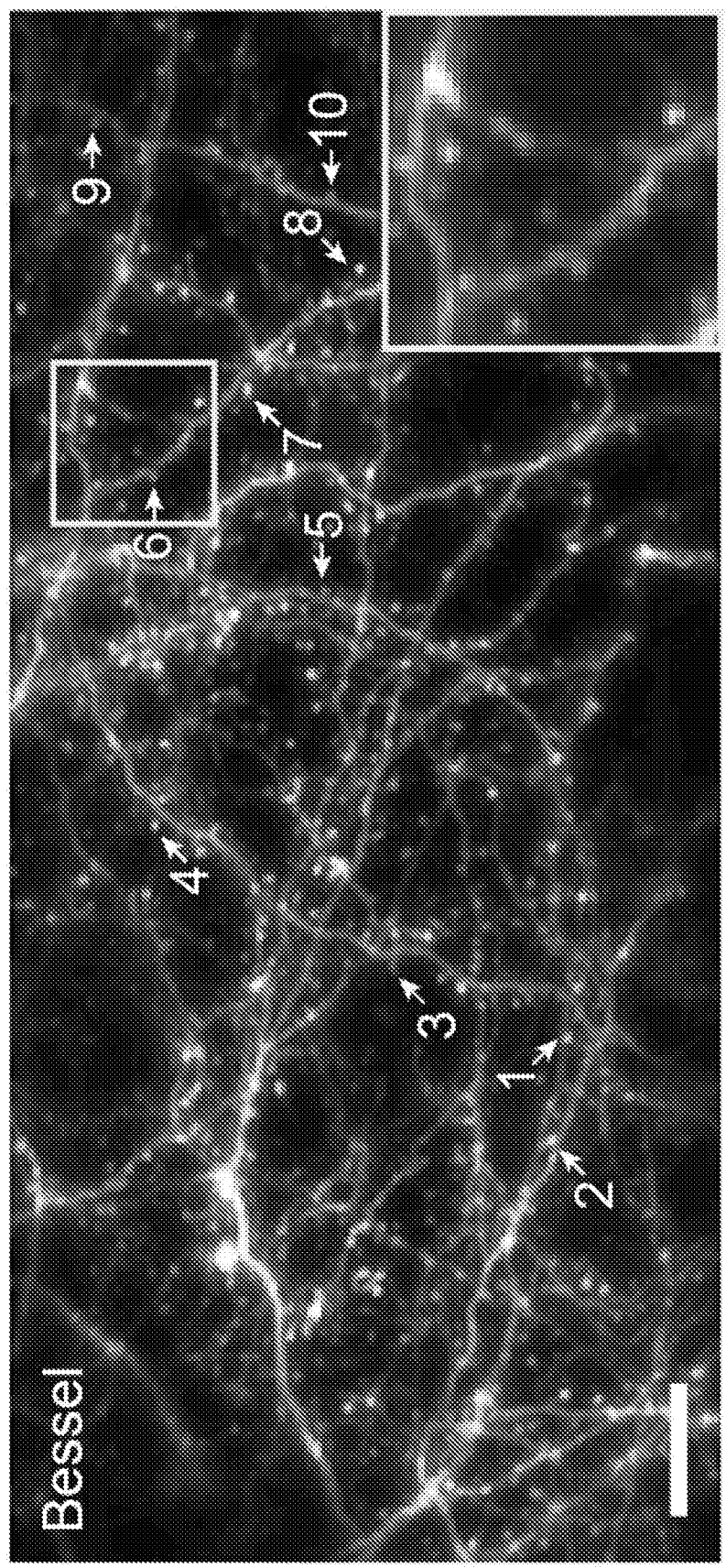
FIG. 6 is a volumetric image of the volume represented in FIG. 5 where the image is obtained by scanning a quasi-Bessel excitation beam in the sample.

To demonstrate the speed and resolution of quasi-Bessel beam volume scanning, sparse GCaMP6s+ neurites (0-60 μm below pia) in the primary visual cortex (V1) of awake mice were imaged. With a Gaussian focus (NA 1.05, axial FWHM 1.4 μm), conventional 3D scanning was used to capture an image stack of a plurality of 2D frames in the z-direction to cover all spines with a volume extending 60 μm in z. FIG. 5 is an image obtained from projecting 60 2D frames obtained with a Gaussian excitation beam onto a single image plane. In contrast, FIG. 6 is an image obtained from scanning the focus of a quasi-Bessel beam having NA 0.4 and an axial FWHM 53 μm in 2D, which captured all the structures shown in FIG. 5 in one frame, thus reducing the data size by approximately a factor of 60. Importantly, with quasi-Bessel beam scanning, the gain in volume imaging speed does not come with a reduction of lateral resolution, as synapses (shown by arrows in FIG. 6) are clearly resolvable even in single frames taken at 30 Hz.

Because of the high axial FWHM of a quasi-Bessel beam, a feature of quasi-Bessel beam scanning as a volumetric imaging tool is its robustness against artifacts induced by axial brain motion. In awake behaving mice, the brain may move both laterally (within the xy plane) and axially (along z). Whereas lateral motions can be corrected post hoc, axial motion correction requires one to constantly image volumes encompassing the entire z motion range, which may vary from 2 μm (in head-fixed running mice) to 15 μm (induced by licking). Because quasit-Bessel foci have an extended axial range for excitation with slow falloff, images taken with quasi-Bessel beam focus scanning are less sensitive to small z displacements of the sample than Gaussian beams. In other words, because a quasi-Bessel beam focus is basically light whose lateral spread remains small (as determined by its NA or lateral resolution) over a large axial propagation distance (as indicated by the axial FWHM), during quasi-Bessel beam focus scanning, a volume is imaged with the axial scan speed being the speed of light. As a result, no postprocessing is needed for registration in z.

Figure 8:
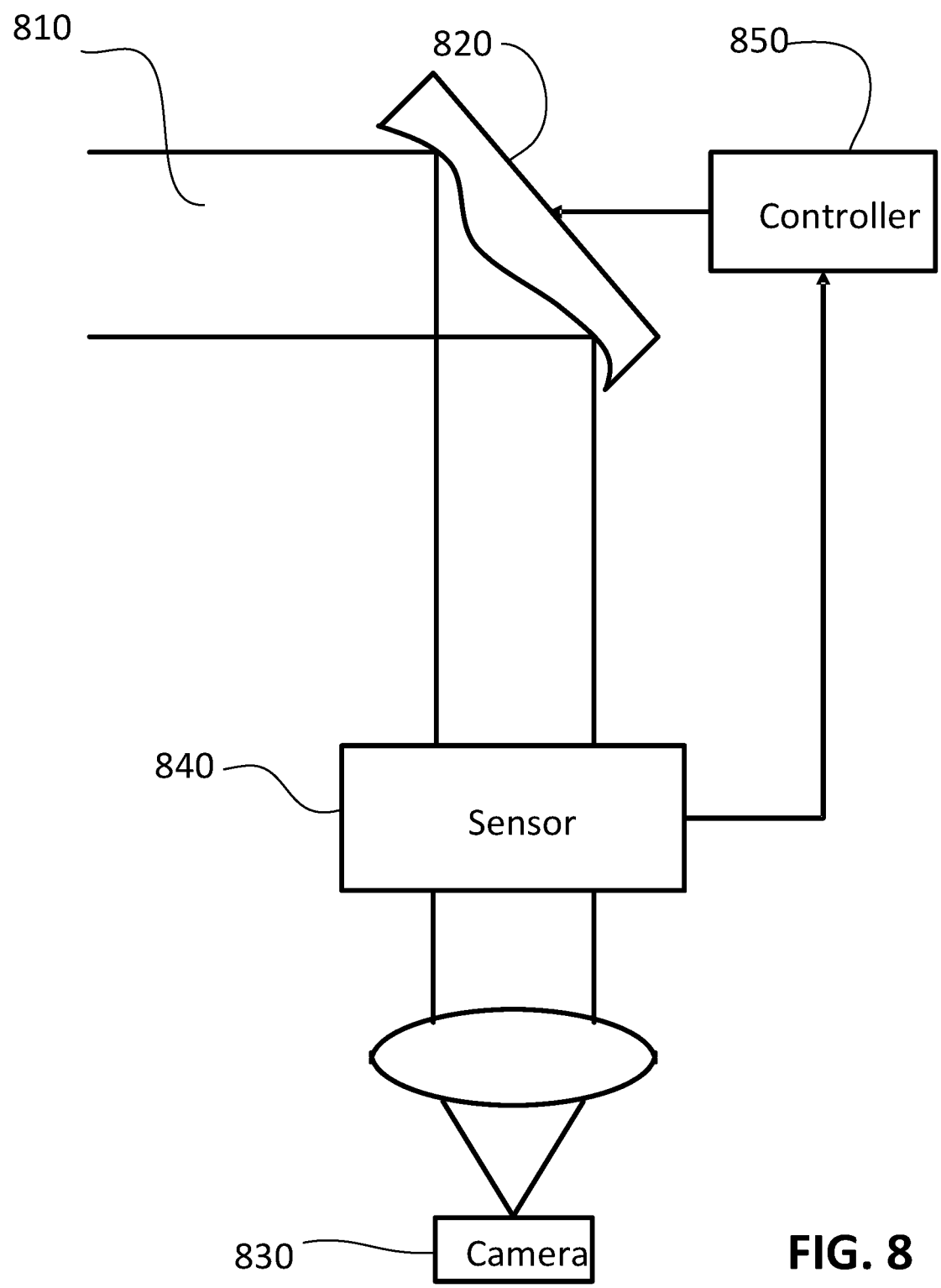
FIG. 8 is a schematic diagram of a microscopy system with adaptive optics.

While use of the quasi-Bessel beam addresses deficiencies of optical systems having small excitation volumes, the performance of the optical system can be significantly degraded by optical aberrations in the optical system or external to the optical system (e.g., caused by the sample itself) that may be unpredictable and possibly changing with time. Adaptive optics (AO) provides a means to reduce wavefront distortions caused by the source of aberration to achieve improved performance. For example, as shown in FIG. 8, the wavefront of a source light beam 810 can be corrected by a wavefront modulator (e.g., a deformable mirror) 820, so that a sharper image can be collected by a camera 830. A sensor 840 is configured to detect a wavefront of the light beam, and the controller 850 is configured to adjust the wavefront modulator 820 to correct the wavefront of the beam accordingly. In AO systems, a wavefront correcting device (e.g., a deformable mirror or a liquid crystal spatial light modulator) contains several to thousands of individually addressable actuators or cells (pixels) to affect the wavefront. There are many possible adaptive optics wavefront modulating elements that can be used in an embodiment of the present invention, a subset of which are shown in FIGS. 9A-9I.

Figure 9A:
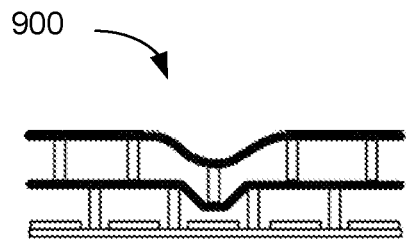
FIGS. 9A-9I are example adaptive optics elements for use in a microscopy system.

For example, FIG. 9A is a schematic diagram of a wavefront modulator 910 that includes a MEMs deformable mirror having a continuous reflective face sheet and a plurality of electrostatic actuators coupled to the face sheet to change a shape of the surface of the face sheet.

Figure 9B:
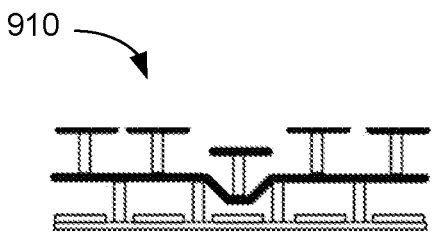

FIG. 9B is a schematic diagram of a wavefront modulator 920 that includes a MEMs deformable mirror having a segmented reflective face sheet and a plurality of electrostatic actuators coupled to segments of the face sheet to change a shape of the surface of the segmented face sheet.

Figure 9C:

FIG. 9C is a schematic diagram of a wavefront modulator 930 that includes a MEMs deformable mirror formed of a single membrane with a plurality of electrostatic actuators coupled to different portions of the membrane to change a shape of the surface of the membrane.

Figure 9D:
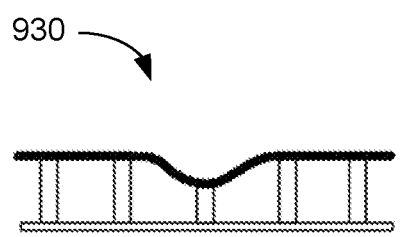

FIG. 9D is a schematic diagram of a wavefront modulator 940 that includes a deformable mirror surface and a plurality of piezoelectric actuators coupled to the deformable mirror change a shape of the surface of the surface.

Figure 9E:
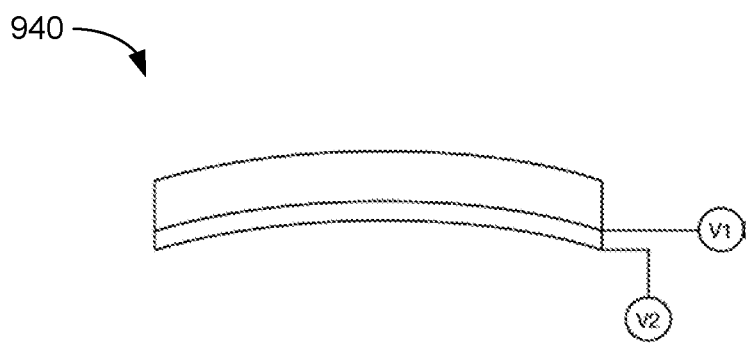

FIG. 9E is a schematic diagram of a wavefront modulator 950 that includes a bimorph deformable mirror having a reflective surface layer coupled to one or more piezoceramic disks having a patterned electrodes, where different voltages applied to the patterned electrodes can cause a change in the shape of the reflective surface layer.

Figures 9F, 9G:
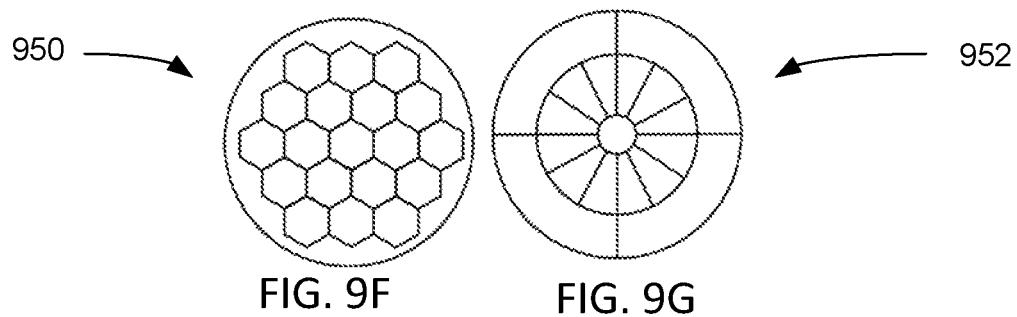

FIG. 9F is a schematic diagram of a wavefront modulator 950 that includes a first pattern of portions of a reflective surface, where the portions are controlled by different actuators. FIG. 9G is a schematic diagram of a wavefront modulator 952 that includes a second pattern of portions of a reflective surface, different from the first pattern, where the portions are controlled by different actuators. The arrangement of the actuators in the adaptive optics wavefront modulating elements can vary depending on the design of the adaptive optics element. Common actuator layouts include grid patterns, honey-comb patterns, concentric circles, radially aligned actuators, circle or arc segment actuator layouts, and others.

Figure 9H:
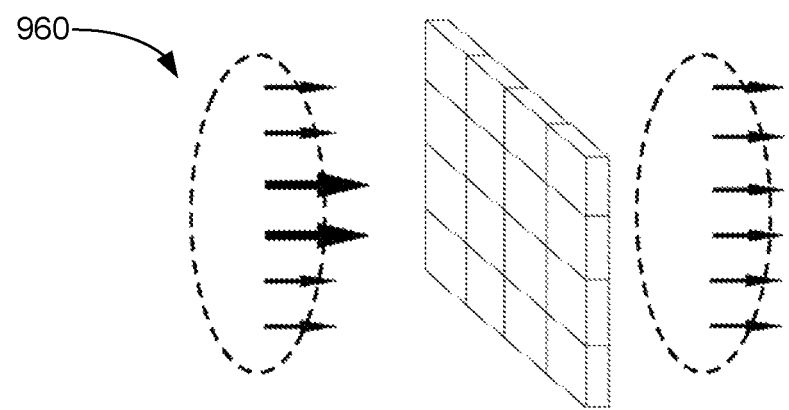

FIG. 9H is a schematic diagram of a wavefront modulator 960 that includes a liquid crystal spatial light modulator having individually addressable elements that can alter the intensity of light reflected from the element.

Figure 9I:
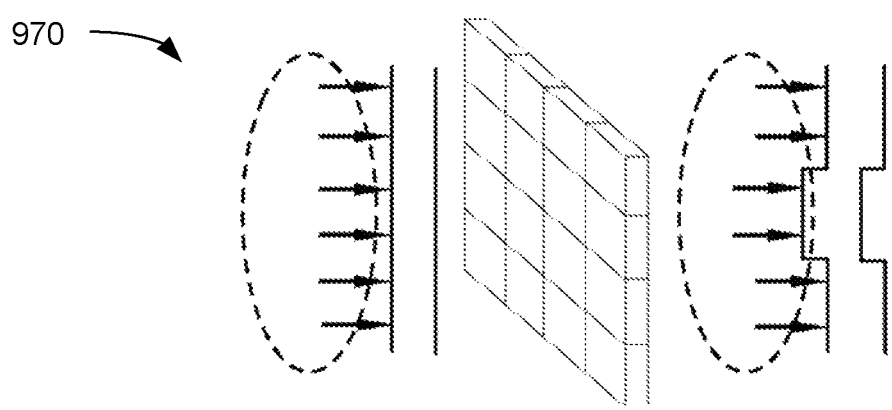

FIG. 9I is a schematic diagram of a wavefront modulator 960 that includes a liquid crystal spatial light modulator having individually addressable elements that can alter the phase of light reflected from the element.

Note that other active and multi actuators or channel optical elements that can affect the wavefront, affect the intensity, or affect both the wavefront and intensity of the light are contemplated as possible embodiments in the present invention.

Undesirable distortions to the wavefront can be corrected or a more preferable wavefront shape generated with the wavefront correcting device integrated in the optical system. In one embodiment of the present invention, adaptive optics is incorporated into the quasi-Bessel beam scanning microscopes described above.

Figure 10:
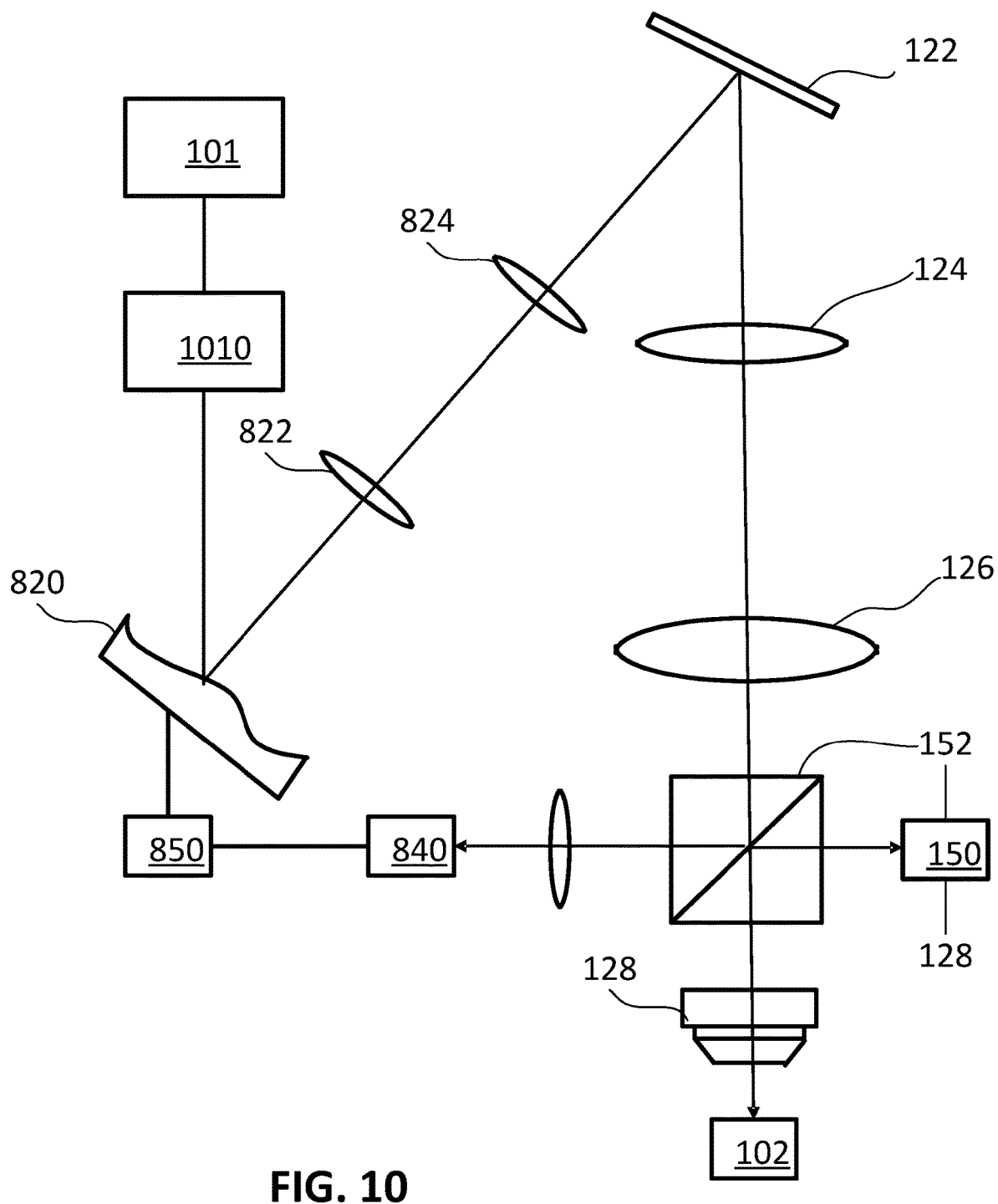
FIG. 10 is a schematic diagram of a microscopy system with quasi-Bessel beam generation and adaptive optics according to an embodiment.

FIG. 10 shows a schematic diagram of a microscopy system with adaptive optics. For simplicity, the details for the optical elements configured for generating a quasi-Bessel beam are encapsulated into a quasi-Bessel beam module 1010. The details of the quasi-Bessel beam generation have been discussed above and not repeated hereafter. As shown in FIG. 10, the light from the light source 101 is converted into a quasi-Bessel beam by the elements encapsulated in module 1010. The quasi-Bessel beam is reflected by a wavefront modulator 820 (e.g., a deformable mirror or a liquid crystal spatial light modulator) to the scanning mirrors 122. It is understood that relay optics 822, 824 may be used to properly image the pupil planes. The beam splitter may receive a portion of the light that is directed from the lens 126 into the objective and/or may receive light emitted from the sample in response to the light focused into the sample and may direct the receive light into the sensor 840 for analysis by the controller 850 that controls the wavefront modulator 820. Note that the arrangement of the optical elements shown in FIG. 10 is a non-limiting illustrative example. It is understood that one or more optical elements may be added, and some optical elements may be omitted or substituted, and that the optical elements may be arranged differently based on specific needs of the microscopy system. In an implementation, the beam splitter 152 reflects a portion of the incoming quasi-Bessel beam onto a sensor 840, and a controller 850 uses the sensed wavefront distortion results from the sensor to adjust the wavefront modulator 820 so as to alter the wavefront of the light that is reflected by the wavefront modulator in such a manner as to compensate for distortions of the light that is imaged into the sample by other elements with which the light interacts and to reduce achieve improved performance of the system. For example, the wavefront modulator 820 can be controlled, such that a wavefront is provided to the back pupil of the objective 128 that compensates for wavefront distortions due to optical elements of the system such that an optimal quasi-Bessel beam can be produced when focused by the objective. In another implementation, the beam splitter 152 reflects a portion of the light emitted from the sample 102 in response to the quasi-Bessel beam focused into the sample onto a sensor 840, and a controller 850 uses the sensed wavefront distortion results from the sensor to adjust the wavefront modulator 820 so as to alter the wavefront of the light that is reflected by the wavefront modulator in such a manner as to compensate for distortions of the light that is imaged into the sample by other elements with which the light interacts and to reduce achieve improved performance of the system. For example, the wavefront modulator 820 can be controlled, such that the wavefront provided to the back pupil of the objective 128 has a wavefunction that compensates for distortions of the imaged light caused by the sample itself to optimize the quasi-Bessel beam provided within the sample.

Figure 11A:
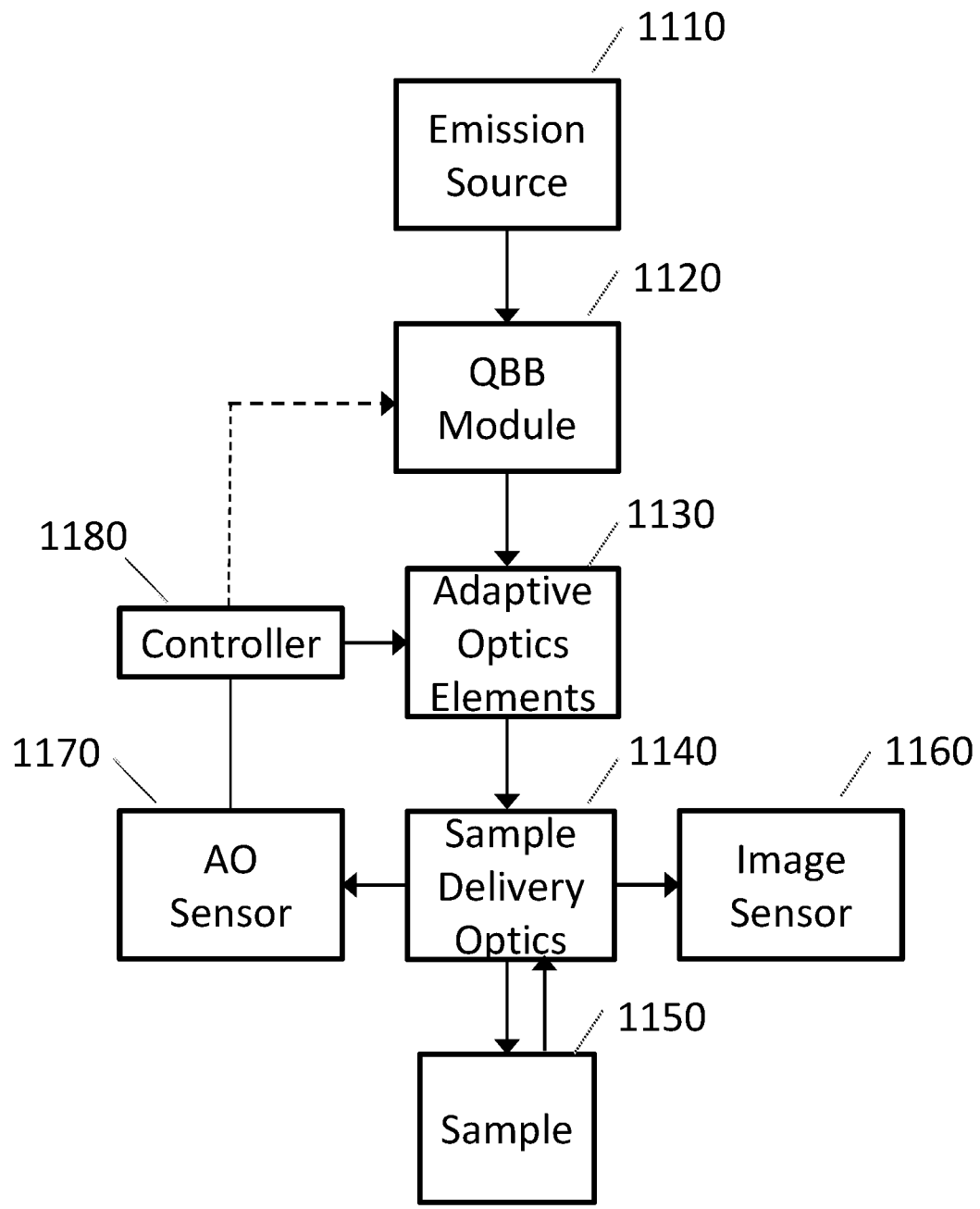
FIGS. 11A-11D are block diagrams of microscopy systems according to various embodiments.

FIG. 11A is a block diagram showing an example embodiment in which the AO sensor 1170 receives light from at least a portion of the sample delivery optics 1140 similar to FIG. 10. An example embodiment in which the AO sensor 1170 receives light from at least a portion of the sample delivery optics 1140 is multiphoton imaging in which the light is collected through the microscope objective, patient interface optics, scan lens, or other sample delivery optics 1140 and imaged by the image sensor 1160.

Figure 11B:
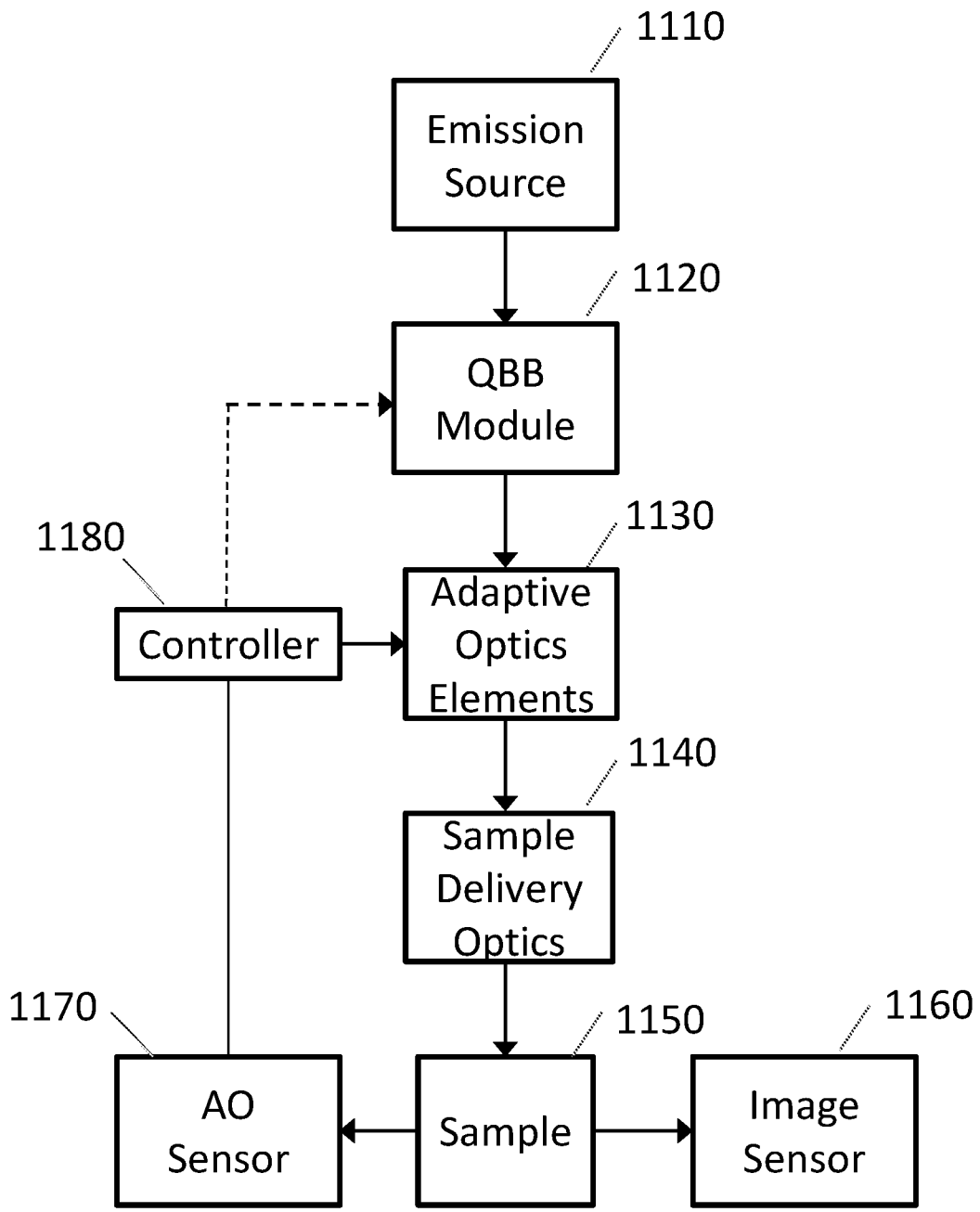

FIG. 11B shows an example embodiment in which the AO sensor 1170 and the image sensor 1160 is located after and/or separate from the sample delivery optics 1140. One example of an embodiment in which the image sensor 1160 is located after the sample delivery optics 1140 would be a multiphoton imaging system in which the image sensor 1160 receive light from the sample 1150 directly, as is sometimes used when imaging thin samples or when detectors are arranged around the sample, but do not share an optical path with the sample delivery optics 1140. In this embodiment, the AO may also reduce wavefront distortion caused by the sample because the AO sensor 1170 receives light produced from an interaction of the quasi-Bessel beam with the sample 1150. It is understood that the positioning of the AO sensor 1170 and image sensor 1160 in FIG. 11B after the sample 710 only indicates the path of the light and does not indicate where the AO sensor 1170 and image sensor 1160 are spatially located relative to the sample 1150 and sample delivery optics 1140 in practice.

Figure 11C:
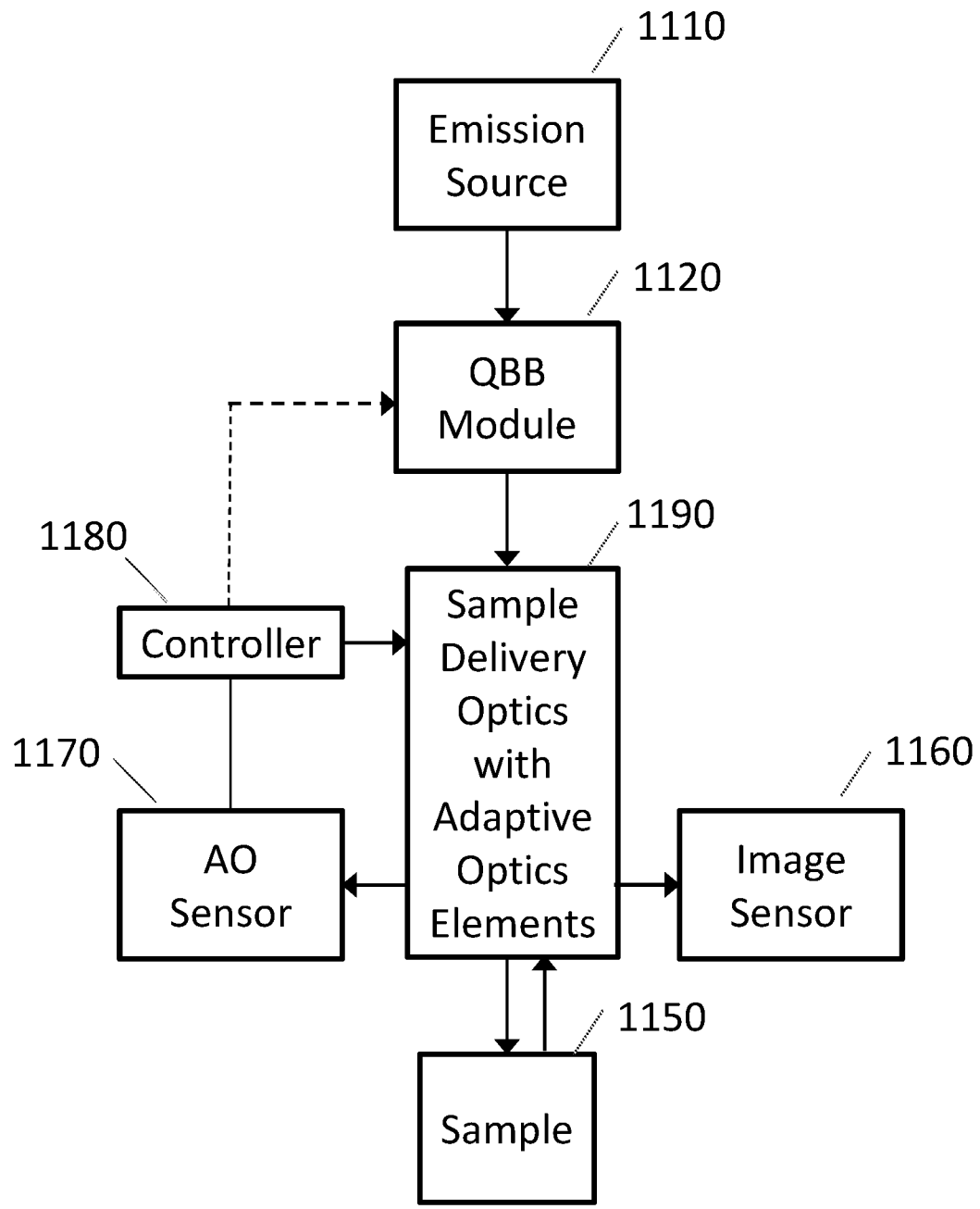

FIGS. 11A and 11B show that the AO elements 1130 is located after the quasi-Bessel beam (QBB) module 1120 and before the sample delivery optics 1140 as illustrative examples. It is understood that the AO elements may be integrated into the quasi-Bessel beam module and/or the sample delivery optics. FIG. 11C shows an embodiment in which the adaptive optics elements and the sample delivery optics are arranged into a single arrangement 1190. For example, in one embodiment, an AO element is located after the lenses 124, 126 of the sample delivery optics shown in FIG. 1. Other arrangements that combine multiple optical elements and/or modules are also contemplated.

If an element of the quasi-Bessel beam module 1120 is adjustable, it may be beneficial to provide feedback to the quasi-Bessel beam module for further adjustment. For example, the position of the lens 714 shown in FIG. 7 may be adjusted based on the sensed wavefront by the AO sensor. FIGS. 11A-11C include an optional feature to further have the controller 1180 adjust an element in the quasi-Bessel beam module 1120 to achieve even better the performance of the system. Thus, the AO sensor provides feedback for both the wavefront adjustment and quasi-Bessel beam generation.

Figure 11D:
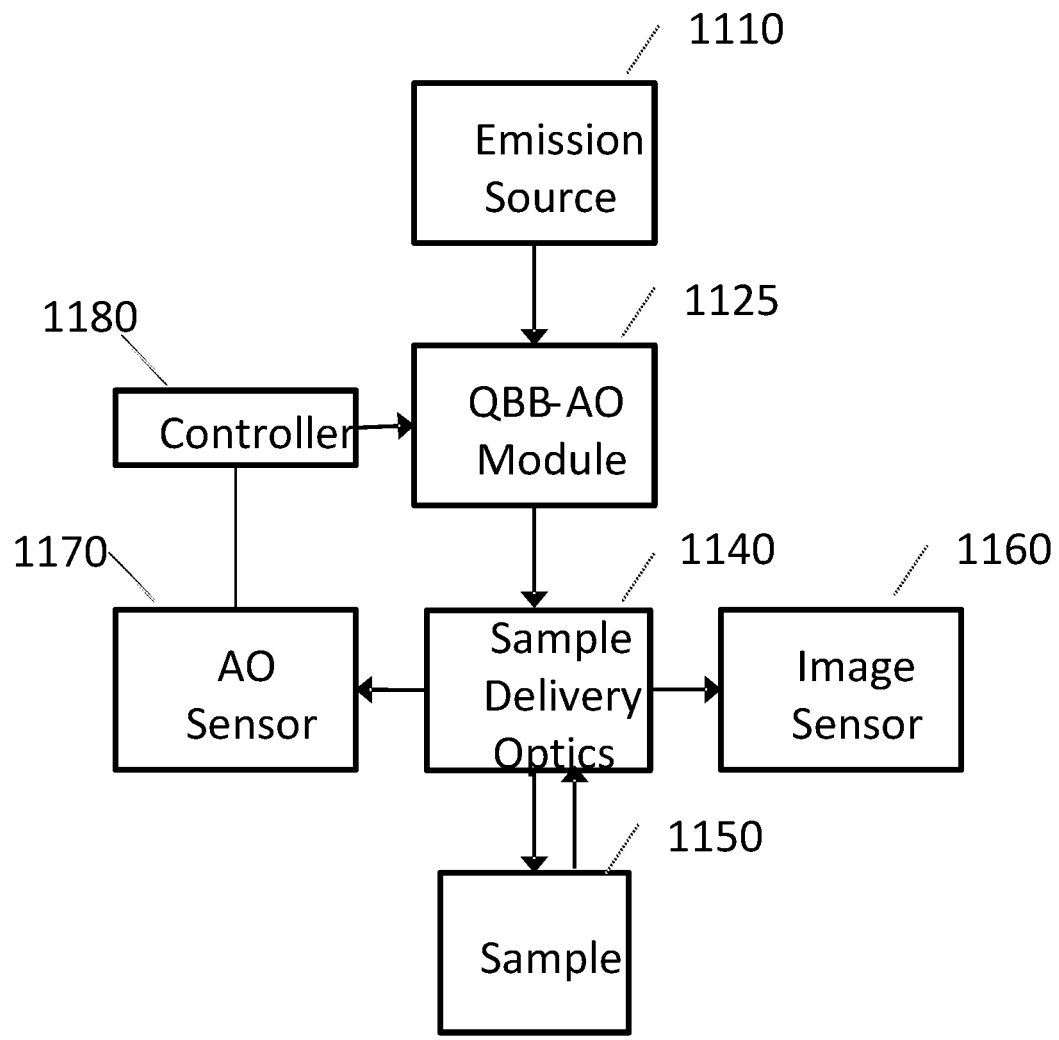

In one embodiment, the quasi-Bessel beam formation and adaptive optics function are integrated into a single SLM. This quasi-Bessel beam-adaptive optics (QBB-AO) module 1125 is shown in FIG. 11D. The QBB-AO module is configured to modify the wavefront to generate a quasi-Bessel beam, and the controller 1180 is configured to control the AO function of the SLM to correct wavefront distortion based on feedback from the AO sensor 1170. In one embodiment, the QBB-AO module is a reflective type SLM. For example, the SLM includes a liquid crystal on a silicon (LCOS) back plane. The SLM can be used to control the amplitude, phase and/or polarization to adjust the wavefront of the output beam.

As a demonstration, using an extended Bessel focus (NA 0.4, axial FWHM 91 µm), we imaged at 30 Hz dendritic branches (180 µm×180 µm×160 µm) of a GCaMP6f+ neuron in the somatosensory cortex (Si) of an awake mouse with quasi-Bessel beam focus scanning. Despite substantial lateral movement, the entire structure stayed within the extended Bessel focus.

We also applied the technique of scanning a quasi-Bessel beam to high-throughput functional mapping of sensory-evoked calcium transients in single spines. Because of their small sizes and three dimensionally distributed locations on dendrites, imaging dendritic spines over large volumes in vivo is technically challenging. With conventional Gaussian focus scanning, multiple imaging planes must be acquired and tiled to cover a single branch. However, with the extended depth of focus offered by a quasi-Bessel beam focus, imaging calcium transients in dendritic spines along multiple dendritic branches could be performed simultaneously.

We first investigated the tuning properties of spines on a L2/3 neuron in V1 of an anesthetized mouse presented with drifting grating stimuli (12 orientations presented with pseudorandom sequences for 10 trials). Conventional Gaussian focus scanning in 3D provided a depth-resolved image stack of GCaMP6s+ spines along dendritic branches 100-160 µm below pia. Scanning a quasi-Bessel beam focus (NA 0.4, axial FWHM 35 µm) in 2D, we resolved these spines in a 102 µm×102 µm×60 µm volume and measured their visually evoked spine-specific calcium transients at 1.5 Hz. Following previous work, we removed transients induced by the occasional back-propagating action potential (BAP) from the calcium signal, and quantified the spine calcium transients as percentage fluorescence change $\Delta F/F$, where $\Delta F = F_{response} - F_{baseline}$, $F = F_{baseline}$. Of all 75 identified dendritic spines, 57.3% (43 spines) exhibited visually evoked activity ($\Delta F/F > 10\%$), with 36 spines also showing significant tuning to grating angles. Representative spines showed large visually evoked transients selective to grating angle but independent of their neighboring dendritic shafts, which showed little responses with no significant tuning preference. We found that spines on the same branch could have different tuning preferences, and the tuning of the BAP-induced calcium transients in dendritic shafts (indicative of somatic tuning) was similar to the histogram of the preferred grating angles of all tuned spines, consistent with previous observations.

As a demonstration that the quasi-Bessel beam scanning module is also compatible with commercial 2PLSM systems, we integrated a quasi-Bessel beam scanning module into a commercial 2PLSM system that was designed to image ferret brains and achieved similar imaging performance and measured calcium transients from dendrites and spines distributed over 72 µm axial range within ferret V1 at 30 Hz and determined the tuning of dendritic spines towards drifting gratings.

In addition to monitoring the activity of neuronal compartments, quasi-Bessel beam focus scanning can also be used to monitor the population dynamics of 3D neural ensembles such as cortical GABAergic neurons. Representing 15-20% of all neurons in neocortex and playing important roles in shaping the functional architecture of cortical networks, these typically inhibitory neurons have been studied with 2PLSM in vivo. Improved labeling strategies (through transgenic mouse strains or post hoc identification via immunohistochemistry) have enabled imaging of specific subtypes of GABAergic neurons in vivo. However, the ensemble dynamics of GABAergic neurons are much less studied. One technical challenge for studying cell-type-specific ensemble activity is caused by their low density in neocortex: a typical 2D image plane may contain <10 GABAergic neurons and even fewer neurons of specific subtypes, making it difficult to measure the activity of large numbers of neurons at the same time.

Using an extended quasi-Bessel beam focus (NA 0.4, axial FWHM 78 μm), we simultaneously captured the calcium transients of up to 71 GCaMP6s+ GABAergic neurons scattered within 256 μm×256 μm×100 μm volumes (0-100, 101-200, 201-300, 301-400 μm below pia) in V1 of quietly awake Gad2-ires-Cre mice. Due to their low density, almost all neurons visible in the Gaussian 3D stacks could be identified in the projected volume view offered by Bessel focus scanning.

We measured how these GABAergic neurons responded to drifting grating stimuli. During experiments, we also monitored the pupil of the mouse, whose size fluctuation reflected brain state. After subtracting the neuropil background from GCaMP6s+ neurites, we found, at all depths, that a substantial fraction of neurons were not visually driven but had calcium transients strongly correlated with the pupil size and with each other. Such activity synchrony persisted in darkness and was also observed using conventional Gaussian focus scanning mode. We found more widespread synchrony for superficial GABAergic neurons than for deeper ones.

Because GABAergic neurons in cortex include several subtypes with distinct properties, we investigated how activity synchrony depended on cell type. We focused on two subtypes that were immuno-reactive for vasoactive intestinal peptide (VIP) and somatostatin (SOM), respectively, because they were known to be involved in cortical state changes as indicated by pupil size. Using transgenic mice (VIP-ires-Cre and SST-ires-Cre) where only VIP+ or SOM+ neurons expressed GCaMP6s, we imaged ensembles of VIP+ and SOM+ neurons using Bessel scanning during visual stimulus presentation. We found that VIP+ neurons had highly synchronized activity that was positively correlated with pupil size. In contrast, responses of SOM+ neurons were more heterogeneous, and on the population level, less synchronized with pupil size.

These observations are in general agreement with known properties of VIP+ and SOM+ neurons. Earlier in vivo studies found that individual VIP+ neurons became active during heightened attention/pupil dilation, consistent with our observation of the large R's between neuronal calcium transients of VIP+ neurons and pupil size. Quasi-Bessel beam focus scanning enabled us to obtain experimental evidence that VIP+ neuron ensembles in cortical volumes have highly synchronized, brain-state-correlated activity (possibly mediated by gap junctions). Given several recent studies showing that VIP+ neurons directly inhibit SOM+ neurons, we expected to see mostly negative correlation between SOM+ neurons and pupil size. However, we found SOM+ neurons to exhibit heterogeneous responses, with some negatively correlated with pupil size (and thus VIP+ neuron activity) while others positively correlated with pupil size. This is consistent with recent in vivo studies, where SOM+ neurons were found to have heterogeneous population responses including those co-active with VIP+ neurons. It is also consistent with the suggestion that SOM+ neurons in SST-ires-Cre mice may include multiple subtypes of inhibitory neurons. The distinct activity patterns of VIP+ and SOM+ neurons may explain the decrease in activity synchrony of GABAergic neurons with depth. Because VIP+ neurons are more abundant in superficial layers whereas SOM+ neurons are more frequently found at larger depths, the correlation coefficients of the mixed GABAergic populations would be expected to decrease with depth, as observed in our experiment.

Additionally, the ability of quasi-Bessel beam focus scanning to monitor the activity of inhibitory neuron ensembles in large volumes, makes it a powerful tool to elucidate how they shape the dynamics of cortical activity during learning as well as during distinct attentional and behavior states.

In addition to being used to study mammalian brains, quasi-Bessel beam focus scanning can also be applied to other specimens. Even for optically transparent brains such as those of zebrafish larvae, where widefield imaging methods have been used to image volumes at high rates, the quasi-Bessel beam approach still offers superior volumetric imaging performance, when the neural ensembles under investigation are distributed sparsely in 3D. One example is the set of spinal projection neurons in the hindbrain of zebrafish larvae. These neurons, which form a stereotyped array in which many cells are uniquely identifiable across individuals, are responsible for the descending control of swimming behaviors, including sensory-evoked escapes. While some of these neurons appear to be dedicated to controlling specific movements, there is evidence for modules that control different kinematic features across behaviors, as well as for more distributed control of swim kinematics.

There does not yet exist an integrated understanding of how this population controls swimming. Since larval swimming occurs in discrete bouts separated by as little as 100 milliseconds, relating activity in this population to behavior requires imaging simultaneously across all the neuronal groups with high temporal resolution using, for example, quasi-Bessel beam focus scanning techniques. We injected Cal520 dextran into the ventral spinal cord of mitfa−/− (nacre) zebrafish. We then examined the calcium dynamics of the retrogradely labeled reticulospinal neurons in paralyzed larvae (7 days post fertilization) in response to a 4-ms mechanical and acoustic stimulus that induces fictive escape behavior. Unlike conventional imaging where neurons at different z planes had to be interrogated separately, a quasi-Bessel beam focus (NA 0.4, axial FWHM 64 μm) enabled us to image the reticulospinal neurons within a 270 μm×270 μm×100 μm volume at 30 Hz. Due to minimal overlap between these neurons when viewed dorsally, all the neurons visible in the conventionally obtained z stack were identifiable in the projected volume view offered by the Bessel focus scan. During nine repeated presentations of the stimulus, most neurons showed stimulus-evoked calcium transients, consistent with previous recordings during escape behavior. Additionally, bursts of activity were observed between stimulus presentations in sets of neurons that were distinct from, but overlapping with, those activated by the acoustic stimulus. The ability to monitor the activity of neurons located at different depths with quasi-Bessel beam scanning simultaneously makes it possible to detect trial-to-trial variations in the ensemble activity and discover neurons with correlated or anti-correlated activity patterns.

The fruit fly (*Drosophila melanogaster*) is an important model organism for the field of neuroscience, and the availability of sophisticated genetic tools and the small size of the fly brain have made it possible to record activity from anywhere inside the brain. We first used quasi-Bessel beam focus scanning to image GCaMP6f$^+$ neurites in UAS-GCaMP6f;33A12-GAL4 flies. Presenting the same drifting grating stimuli described above to head-fixed flies, we monitored the calcium dynamics of a volume of neurites comprising most of the central complex (190 µm×95 µm×60 µm), a highly structured neuropil in the center of the fly brain, at a rate of 2.5 Hz, using a quasi-Bessel beam focus (NA 0.4, axial FWHM 35 µm) scanning. The imaged volume contained fine neurites surrounding the ellipsoid body (a substructure of the central complex), whose activity can be captured by a single Bessel frame. We found that the columnar neuron neurites within the ellipsoid body on either side of the central complex midline had strongly anti-correlated activity, which was not synchronized to the presentation of visual stimulation. In contrast, two neuronal processes above the ellipsoid body on both sides of the midline were strongly activated by drifting grating stimuli with no preference with respect to grating orientation.

We also applied quasi-Bessel beam focus scanning to fly brains with pan-neuronal expression of GCaMP6f (UAS-GCaMP6f;57C10-GAL4). Scanning with an extended quasi-Bessel beam focus (NA 0.4, axial FWHM 78 µm) allowed us to measure visually evoked responses from a 307 µm×216 µm×100 µm volume, ~25% of the entire adult brain, at 3.6 Hz. Interestingly, the pixels with the strongest responses to grating stimuli in our imaging volume fell within the area of the mushroom bodies, structures mostly known for olfactory learning and memory but not for visually driven responses in *Drosophila*. Because Bessel focus scanning cannot resolve structures along the z direction, we switched the microscope to conventional scanning with a Gaussian focus to confirm these responses. Placing the Gaussian focus within the mushroom bodies and presenting the fly with the same grating stimuli, we again observed visually driven responses in the mushroom bodies. Both the axially averaged responses obtained via Bessel focus scanning and the optically sectioned responses obtained via conventional scanning shared similar features: calcium transients were evoked by both the appearance of new stationary gratings (data points within the purple stripes) and the drifting movement of the gratings (data points outside the purple stripes), and in both cases, the transients rapidly decayed with time. Our observation that mushroom bodies exhibit visually evoked responses is consistent with the recent discovery of Kenyon cells in the mushroom body that selectively responds to visual stimulation. Given that the adult fly brain has a lateral extension (590 µm×340 µm) that is within the typical field of view of 2PLSM and a thickness (120 µm) that is within the axial extent of our quasi-Bessel beam foci, quasi-Bessel beam focus scanning shows great promise as a method for rapid surveys of stimulus- or behavior-related neural activity in the entire fly brain.

In addition to using scanning of an excitation beam having a quasi-Bessel beam focus within a sample to cause the emission of light from the sample, which light can be detected to image the sample, scanning of a quasi-Bessel beam focus within a sample can be used for other purposes as well. For example, scanning of a quasi-Bessel beam focus can be used in the field of optogenetics to cause or inhibit an event in a living sample by providing light to the sample. In a particular example, optogenetics can be used to study the neural circuit underpinnings of behavior through the use of microbial opsin proteins that directly elicit electrical current across cellular membranes in response to light. Specific opsin gene expression can be targeted to well-defined cellular elements in the brain, and then light can be provided to the targeted elements to trigger or to inhibit a cellular response, due to the opsin protein being activated by the light and causing an electrical current across the cellular membrane.

With the use of light provided to a sample with a quasi-Bessel beam focus, such that the axial FWHM of the beam is relatively long (e.g., greater than 15 microns) and the lateral FWHM of the beam is small (e.g., below one micron), fast volumetric activation of a structure can be accomplished. For example, photoactivation of structures within a volume of size 50 µm×50 µm×50 µm can be accomplished much faster using a quasi-Bessel beam than using a Gaussian beam when the quasi-Bessel beam and the Gaussian beam have the same lateral FWHM and the same intensity. Thus, if many structures (e.g., opsin proteins) need to be activated in a short time period to cause or to inhibit a desired event within the cell, the long axial FWHM of the quasi-Bessel beam provides a beam that can target large volumes in a short time period.

Scanning of a quasi-Bessel beam focus can also be used in activation of photolabile protecting groups on biomolecules or "caged" biomolecules. Caged biomolecules are biologically inert and are split from the protecting group or caging group through photolysis, resulting in a biologically active biomolecule. The multi-photon activating capability of a quasi-Bessel beam focus allows for tightly controlled activation of the biomolecule over time and space. For example, caged Nicotine, Glutamate, and Gamma-Amino Butyric Acid molecules have been employed in research over the past decade for precise targeting of molecules to modulate neurons. Optogenetics and molecular activation can be used in therapeutic applications as well, such as for treatment of a neurological disorder. For example, blindness, Parkinson's disease, or schizophrenia can be treated by optical targeting of biomolecules or synthetic molecules. The scanning of quasi-Bessel beams to provide activation light in these applications allows the possibility of providing activation light over large volumes in short timescales, due to the extended axial FWHM of the quasi-Bessel beam.

Implementations of the various techniques described herein may be implemented in digital electronic circuitry, or in computer hardware, firmware, software, or in combinations of them. Implementations may implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by or incorporated in special purpose logic circuitry.

To provide for interaction with a user, implementations may be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the implementations.

What is claimed is:

1. A scanning microscope comprising:
    a light source for generating a light beam having a wavelength, $\lambda$;
    beam-forming optics configured for receiving the light beam and generating a quasi-Bessel excitation beam that is directed into a sample, wherein the quasi-Bessel beam has a lateral FWHM and an axial FWHM that is greater than ten times the lateral FWHM, the beam-forming optics including an excitation objective having an axis oriented in a first direction, wherein the beam forming optics include a reflective spatial light modulator (SLM) configured to receive the light beam and to generate the quasi-Bessel beam in the sample;
    beam scanning optics configured for scanning the quasi-Bessel beam in one or more directions that are substantially perpendicular to the first direction;
    a sensor configured for sensing a wavefront distortion in the quasi-Bessel beam;
    a wavefront modulator configured for adjusting a wavefront of the quasi-Bessel beam based on the sensed wavefront distortion; and
    a detector configured for detecting signal light received from positions within the sample that are illuminated by the quasi-Bessel beam,
    wherein the signal light is generated in response to an interaction of the excitation beam with the sample, and
    wherein the signal light is imaged, at least in part, by the excitation objective, onto the detector.

2. The scanning microscope of claim 1, wherein the wavelength $\lambda$ is selected such that the signal light is generated by a multi-photon excitation process when the excitation beam interacts with the sample.

3. The scanning microscope of claim 2, wherein the multi-photon excitation process includes a three-photon excitation process.

4. The scanning microscope of claim 1, wherein the signal light is generated by a non-linear signal generation process when the excitation beam interacts with the sample.

5. The scanning microscope of claim 4, wherein the signal light has a wavelength, $\lambda_S$, that is less than $\lambda$.

6. The scanning microscope of claim 5, wherein $\lambda_S$ is equal to $\lambda/3$.

7. The scanning microscope of claim 4, wherein the signal light is generated through a second-order harmonic generation process and wherein the signal light has a wavelength, $\lambda_S$, that is less than $\lambda$.

8. The scanning microscope of claim 4, wherein the signal light is generated through a third-order harmonic generation process and wherein the signal light has a wavelength, $\lambda_S$, that is less than $\lambda$.

9. A method of imaging a sample, the method comprising:
    receiving a light beam having a wavelength, $\lambda$, and
    transforming the received light beam into a quasi-Bessel excitation beam propagating in a first direction in the sample, wherein the quasi-Bessel beam has a lateral FWHM and an axial FWHM that is greater than ten times the lateral FWHM, wherein transforming the received light beam into the quasi-Bessel includes reflecting the received light beam off a spatial light modulator (SLM) that modifies a wavefront of the received light beam;
    scanning the quasi-Bessel beam in one or more directions that are substantially perpendicular to the first direction;
    sensing a wavefront distortion in the quasi-Bessel beam;
    adjusting a wavefront of the quasi-Bessel beam based on the sensed wavefront distortion; and
    detecting signal light received from positions within the sample that are illuminated by the quasi-Bessel beam, wherein the signal light is generated in response to an interaction of the excitation beam with the sample, and wherein the quasi-Bessel beam is provided through an excitation objective to the sample, and wherein the detected signal light is received though the excitation objective; and
    generating an image of the sample based on the detected signal light.

10. The method of claim 9, wherein the wavelength $\lambda$ is selected such that the signal light is generated by a multi-photon excitation process when the excitation beam interacts with the sample.

11. The method of claim 10, wherein the multi-photon excitation process includes a three-photon excitation process.

12. The method of claim 9, wherein the signal light is generated by a non-linear signal generation process when the excitation beam interacts with the sample.

13. The method of claim 12, wherein the signal light has a wavelength, $\lambda_S$, that is less than $\lambda$.

14. The method of claim 13, wherein $\lambda_S$ is equal to $\lambda/3$.

15. The method of claim 12, wherein the signal light is generated through a second-order harmonic generation process and wherein the signal light has a wavelength, $\lambda_S$, that is less than $\lambda$.

16. The method of claim 12, wherein the signal light is generated through a third-order harmonic generation process and wherein the signal light has a wavelength, $\lambda_S$, that is less than $\lambda$.

17. A scanning microscope comprising:
- a light source for generating a light beam having a wavelength, $\lambda$;
- beam-forming optics configured for receiving the light beam and generating a quasi-Bessel excitation beam that is directed into a sample, wherein the quasi-Bessel beam has a lateral FWHM and an axial FWHM that is greater than ten times the lateral FWHM, the beam-forming optics including an excitation objective having an axis oriented in a first direction, wherein the beam forming optics include a reflective spatial light modulator (SLM) configured to receive the light beam and to generate the quasi-Bessel beam in the sample;
- a sensor configured for sensing a wavefront distortion in the quasi-Bessel beam, wherein the SLM is further configured to adjust a wavefront of the quasi-Bessel beam based on the sensed wavefront distortion;
- beam scanning optics configured for scanning the quasi-Bessel beam in one or more directions that are substantially perpendicular to the first direction; and
- a detector configured for detecting signal light received from positions within the sample that are illuminated by the quasi-Bessel beam,
- wherein the signal light is generated in response to an interaction of the excitation beam with the sample, and
- wherein the signal light is imaged, at least in part, by the excitation objective, onto the detector.

18. The scanning microscope of claim 17, wherein the wavelength $\lambda$ is selected such that the signal light is generated by a multi-photon excitation process when the excitation beam interacts with the sample.

19. The scanning microscope of claim 18, wherein the multi-photon excitation process includes a three-photon excitation process.

20. The scanning microscope of claim 17, wherein the signal light is generated by a non-linear signal generation process when the excitation beam interacts with the sample.

21. The scanning microscope of claim 20, wherein the signal light has a wavelength, $\lambda_S$, that is less than $\lambda$.

22. The scanning microscope of claim 21, wherein $\lambda_S$ is equal to $\lambda/3$.

23. The scanning microscope of claim 20, wherein the signal light is generated through a second-order harmonic generation process and wherein the signal light has a wavelength, $\lambda_S$, that is less than $\lambda$.

24. The scanning microscope of claim 20, wherein the signal light is generated through a third-order harmonic generation process and wherein the signal light has a wavelength, $\lambda_S$, that is less than $\lambda$.

25. A method of imaging a sample, the method comprising:
- receiving a light beam having a wavelength, $\lambda$, and
- transforming the received light beam into a quasi-Bessel excitation beam propagating in a first direction in the sample, wherein the quasi-Bessel beam has a lateral FWHM and an axial FWHM that is greater than ten times the lateral FWHM, wherein transforming the received light beam into the quasi-Bessel includes reflecting the received light beam off a spatial light modulator (SLM) that modifies a wavefront of the received light beam;
- sensing a wavefront distortion in the quasi-Bessel beam;
- adjusting, by the SLM, a wavefront of the quasi-Bessel beam based on the sensed wavefront distortion;
- scanning the quasi-Bessel beam in one or more directions that are substantially perpendicular to the first direction;
- detecting signal light received from positions within the sample that are illuminated by the quasi-Bessel beam, wherein the signal light is generated in response to an interaction of the excitation beam with the sample, and wherein the quasi-Bessel beam is provided through an excitation objective to the sample, and wherein the detected signal light is received though the excitation objective; and
- generating an image of the sample based on the detected signal light.

26. The method of claim 25, wherein the wavelength $\lambda$ is selected such that the signal light is generated by a multi-photon excitation process when the excitation beam interacts with the sample.

27. The method of claim 26, wherein the multi-photon excitation process includes a three-photon excitation process.

28. The method of claim 25, wherein the signal light is generated by a non-linear signal generation process when the excitation beam interacts with the sample.

29. The method of claim 28, wherein the signal light has a wavelength, $\lambda_S$, that is less than $\lambda$.

30. The method of claim 29, wherein $\lambda_S$ is equal to $\lambda/3$.

31. The method of claim 28, wherein the signal light is generated through a second-order harmonic generation process and wherein the signal light has a wavelength, $\lambda_S$, that is less than $\lambda$.

32. The method of claim 28, wherein the signal light is generated through a third-order harmonic generation process and wherein the signal light has a wavelength, $\lambda_S$, that is less than $\lambda$.

* * * * *

UNITED STATES PATENT AND TRADEMARK OFFICE
CERTIFICATE OF CORRECTION

| | |
|---|---|
| PATENT NO. | : 11,237,371 B2 |
| APPLICATION NO. | : 16/949196 |
| DATED | : February 1, 2022 |
| INVENTOR(S) | : Ji et al. |

It is certified that error appears in the above-identified patent and that said Letters Patent is hereby corrected as shown below:

On the Title Page

On Page 2, Column 2, item (56), under "OTHER PUBLICATIONS", Line 11, delete "1307-1132." and insert -- 1307-1312. --, therefor.

On Page 2, Column 2, item (56), under "OTHER PUBLICATIONS", Line 56, delete "Multi plane" and insert -- Multi-plane --, therefor.

Signed and Sealed this
Twenty-third Day of August, 2022

Katherine Kelly Vidal
*Director of the United States Patent and Trademark Office*